United States Patent
Handique et al.

(10) Patent No.: US 9,404,864 B2
(45) Date of Patent: Aug. 2, 2016

(54) SYSTEM FOR IMAGING CAPTURED CELLS

(71) Applicant: DeNovo Sciences, Inc., Plymouth, MI (US)

(72) Inventors: Kalyan Handique, Plymouth, MI (US); Kyle Gleason, Plymouth, MI (US); Christopher Siemer, Plymouth, MI (US); Priyadarshini Gogoi, Plymouth, MI (US); Saedeh Sepehri Javdani, Plymouth, MI (US); Gene Parunak, Plymouth, MI (US); Aaron Kehrer, Plymouth, MI (US); Jon Meines, Plymouth, MI (US)

(73) Assignee: DeNovo Sciences, Inc., Plymouth, MI (US)

( * ) Notice: Subject to any disclaimer, the term of this patent is extended or adjusted under 35 U.S.C. 154(b) by 247 days.

(21) Appl. No.: 14/208,458

(22) Filed: Mar. 13, 2014

(65) Prior Publication Data
US 2014/0273194 A1    Sep. 18, 2014

Related U.S. Application Data

(60) Provisional application No. 61/902,431, filed on Nov. 11, 2013, provisional application No. 61/779,090, filed on Mar. 13, 2013.

(51) Int. Cl.
*G01N 21/00* (2006.01)
*G01N 21/64* (2006.01)

(52) U.S. Cl.
CPC ........ *G01N 21/6428* (2013.01); *G01N 21/6458* (2013.01)

(58) Field of Classification Search
CPC ................................................ G01N 21/6428
See application file for complete search history.

(56) References Cited

U.S. PATENT DOCUMENTS

| 644,134 A | 2/1900 | Gastineau |
|---|---|---|
| 4,551,435 A | 11/1985 | Liberti et al. |

(Continued)

FOREIGN PATENT DOCUMENTS

| WO | 03035909 A2 | 5/2003 |
|---|---|---|
| WO | 2006098696 A1 | 9/2006 |

OTHER PUBLICATIONS

Lindstrom, Sara (Royal Institute of Technology, Stockholm, Sweden, 2009, pp. 1-80).

(Continued)

*Primary Examiner* — Jill Warden
*Assistant Examiner* — Brittany Fisher
(74) *Attorney, Agent, or Firm* — Jeffrey Schox; Ivan Wong

(57) ABSTRACT

A system for imaging captured cells comprising: an illumination module configured to illuminate a target object; a platform configured to position the target object in relation to the illumination module; a filter module configured to filter light transmitted to the target object and/or to filter light received from the target object, an optical sensor configured to receive light from the target object and to generate image data; and a focusing and optics module configured to manipulate light transmitted to the optical sensor. The system can further comprise one or more of: a control system configured to control at least one of the illumination module, the platform, the focusing and optics module, the filter module, and the optical sensor; a tag identifying system configured to identify and communicate tag information from system elements; a thermal control module configured to adjust temperature parameters of the system; and an image stabilization module.

18 Claims, 12 Drawing Sheets

(56) References Cited

U.S. PATENT DOCUMENTS

| | | | |
|---|---|---|---|
| 4,710,635 A * | 12/1987 | Chupp | G01N 15/1427 250/461.1 |
| 5,266,269 A | 11/1993 | Niiyama et al. | |
| 5,491,343 A * | 2/1996 | Brooker | G01N 21/6428 250/458.1 |
| 5,851,488 A * | 12/1998 | Saul | G01N 21/645 422/67 |
| 5,883,370 A | 3/1999 | Walker et al. | |
| 5,888,370 A | 3/1999 | Becker et al. | |
| 5,993,630 A | 11/1999 | Becker et al. | |
| 5,993,632 A | 11/1999 | Becker et al. | |
| 6,016,712 A | 1/2000 | Warden et al. | |
| 6,127,177 A | 10/2000 | Toner et al. | |
| 6,133,030 A | 10/2000 | Bhatia et al. | |
| 6,150,180 A | 11/2000 | Parce et al. | |
| 6,174,683 B1 | 1/2001 | Hahn | |
| 6,221,663 B1 | 4/2001 | Bhatia et al. | |
| 6,228,624 B1 | 5/2001 | Terstappen | |
| 6,287,832 B1 | 9/2001 | Becker et al. | |
| 6,365,362 B1 | 4/2002 | Terstappen et al. | |
| 6,410,724 B1 | 6/2002 | Dejean et al. | |
| 6,433,134 B1 | 8/2002 | Patron et al. | |
| 6,563,634 B2 * | 5/2003 | Shimada | G02B 21/241 359/368 |
| 6,623,983 B1 | 9/2003 | Terstappen et al. | |
| 6,641,708 B1 | 11/2003 | Becker et al. | |
| 6,645,731 B2 | 11/2003 | Terstappen et al. | |
| 6,692,952 B1 | 2/2004 | Braff et al. | |
| 6,790,330 B2 | 9/2004 | Gascoyne et al. | |
| 6,861,259 B2 | 3/2005 | Columbus | |
| 6,960,449 B2 | 11/2005 | Wang et al. | |
| 7,172,866 B2 | 2/2007 | Hahn et al. | |
| 7,198,901 B1 | 4/2007 | Rachlin | |
| 7,217,520 B2 | 5/2007 | Tsinberg et al. | |
| 7,238,521 B2 | 7/2007 | Hahn et al. | |
| 7,258,990 B2 | 8/2007 | Falcovitz-Gerassi et al. | |
| 7,294,468 B2 | 11/2007 | Bell et al. | |
| 7,316,897 B2 | 1/2008 | Bisconte de Saint Julien et al. | |
| 7,332,288 B2 | 2/2008 | Terstappen et al. | |
| 7,439,062 B2 | 10/2008 | Bhatt et al. | |
| 7,449,558 B2 | 11/2008 | Yao et al. | |
| 7,449,778 B2 | 11/2008 | Sander | |
| 7,507,528 B2 | 3/2009 | Albert et al. | |
| 7,595,157 B2 | 9/2009 | Tsinberg | |
| 7,597,528 B2 | 10/2009 | Rodi | |
| 7,604,777 B2 | 10/2009 | Columbus | |
| 7,638,464 B2 | 12/2009 | Fagnani et al. | |
| 7,695,956 B2 | 4/2010 | Tsinberg et al. | |
| 7,763,704 B2 | 7/2010 | Ding et al. | |
| 7,815,863 B2 | 10/2010 | Kagan et al. | |
| 7,858,757 B2 | 12/2010 | Hollmann et al. | |
| 7,863,012 B2 | 1/2011 | Rao et al. | |
| 7,901,950 B2 | 3/2011 | Connelly et al. | |
| 7,964,349 B2 | 6/2011 | Bell et al. | |
| 8,008,032 B2 | 8/2011 | Forsyth et al. | |
| 8,013,298 B2 | 9/2011 | Khursheed | |
| 8,021,614 B2 | 9/2011 | Huang et al. | |
| 8,103,080 B2 | 1/2012 | George et al. | |
| 8,105,769 B2 | 1/2012 | Bell et al. | |
| 8,105,780 B2 | 1/2012 | Su et al. | |
| 8,131,053 B2 * | 3/2012 | Ortyn | G01N 15/147 356/326 |
| 8,158,410 B2 | 4/2012 | Tang et al. | |
| 8,175,371 B2 | 5/2012 | George et al. | |
| 8,186,913 B2 | 5/2012 | Toner et al. | |
| 8,293,524 B2 | 10/2012 | Ionescu-Zanetti et al. | |
| 8,304,230 B2 | 11/2012 | Toner et al. | |
| 8,329,422 B2 | 12/2012 | Rao et al. | |
| 8,372,579 B2 | 2/2013 | Toner et al. | |
| 8,372,584 B2 | 2/2013 | Shoemaker et al. | |
| 8,406,498 B2 * | 3/2013 | Ortyn | G01N 15/147 382/133 |
| 8,465,916 B2 | 6/2013 | Bell et al. | |
| 2002/0119482 A1 | 8/2002 | Nelson et al. | |
| 2002/0192808 A1 * | 12/2002 | Gambini | G01N 21/274 435/287.2 |
| 2003/0138941 A1 | 7/2003 | Gong et al. | |
| 2004/0160599 A1 * | 8/2004 | Hamamatsu | G01N 21/8806 356/237.2 |
| 2004/0229349 A1 | 11/2004 | Daridon | |
| 2004/0248318 A1 | 12/2004 | Weinberger et al. | |
| 2005/0001176 A1 * | 1/2005 | Loney | G01N 21/6428 250/458.1 |
| 2005/0118640 A1 * | 6/2005 | Kureshy | G01N 21/253 435/7.1 |
| 2006/0128006 A1 | 6/2006 | Gerhardt et al. | |
| 2007/0111302 A1 | 5/2007 | Handique et al. | |
| 2008/0014589 A1 | 1/2008 | Link et al. | |
| 2008/0068588 A1 * | 3/2008 | Hess | G01N 21/6458 356/36 |
| 2008/0182273 A1 | 7/2008 | Hansen et al. | |
| 2008/0206751 A1 | 8/2008 | Squirrell et al. | |
| 2009/0061450 A1 | 3/2009 | Hunter | |
| 2009/0081773 A1 | 3/2009 | Kaufman | |
| 2009/0153844 A1 | 6/2009 | Peter et al. | |
| 2010/0120077 A1 | 5/2010 | Daridon | |
| 2010/0210009 A1 | 8/2010 | Willson et al. | |
| 2010/0304485 A1 | 12/2010 | Karnik et al. | |
| 2010/0304978 A1 | 12/2010 | Deng et al. | |
| 2011/0045994 A1 | 2/2011 | Voldman et al. | |
| 2011/0117634 A1 | 5/2011 | Halamish et al. | |
| 2011/0143964 A1 | 6/2011 | Zhou et al. | |
| 2011/0227558 A1 | 9/2011 | Mannion et al. | |
| 2012/0071355 A9 | 3/2012 | Cooney | |
| 2012/0129190 A1 | 5/2012 | Chiu et al. | |
| 2012/0194805 A1 * | 8/2012 | Ness | G01N 21/05 356/213 |
| 2013/0244906 A1 | 9/2013 | Collins | |

OTHER PUBLICATIONS

Sugio et al. (Sensors and Actuators, B99, 2004, pp. 156-162).

Guo, P. et al. Microfluidic capture and release of bacteria in a conical nanopore array. LabChip. vol. 12, p. 558-561, 2012, published online Nov. 2011.

\* cited by examiner

SYSTEM FOR IMAGING CAPTURED CELLS

CROSS-REFERENCE TO RELATED APPLICATIONS

This application claims the benefit of U.S. Provisional Application Ser. No. 61/902,431, filed on 11 Nov. 2013, and U.S. Provisional Application Ser. No. 61/779,090, filed on 13 Mar. 2013, which are both incorporated herein in their entirety by this reference.

TECHNICAL FIELD

This invention relates generally to the cellular analysis field, and more specifically to a new and useful system for imaging captured cells.

BACKGROUND

With an increased interest in cell-specific drug testing, diagnosis, and other assays, systems that allow for individual cell isolation, identification, and retrieval are becoming more desirable within the field of cellular analysis. Furthermore, with the onset of personalized medicine, low-cost, high fidelity cellular sorting systems are becoming highly desirable. However, preexisting cell capture systems and systems to image captured cells suffer from various shortcomings that prevent widespread adoption for cell-specific testing. For example, flow cytometry requires that the cell be simultaneously identified and sorted, and limits cell observation and imaging to a single instance. Flow cytometry thus fails to allow for multiple analyses of the same cell, and does not permit arbitrary cell subpopulation sorting. Conventional microfluidic devices fail to allow for subsequent cell removal without cell damage, which hinders further analysis and imaging of isolated cells. Cellular filters can separate sample components based on size without significant cell damage, but suffer from clogging and do not allow for specific cell identification, isolation, and retrieval. Current systems for capturing cells and imaging/analyzing captured cells are thus severely limited.

Thus, there is a need in the cellular analysis field to create a new and useful system for imaging captured cells or other features of a biological sample at an imaging substrate. This invention provides such a new and useful system.

DESCRIPTION OF THE PREFERRED EMBODIMENTS

Figure 1A:
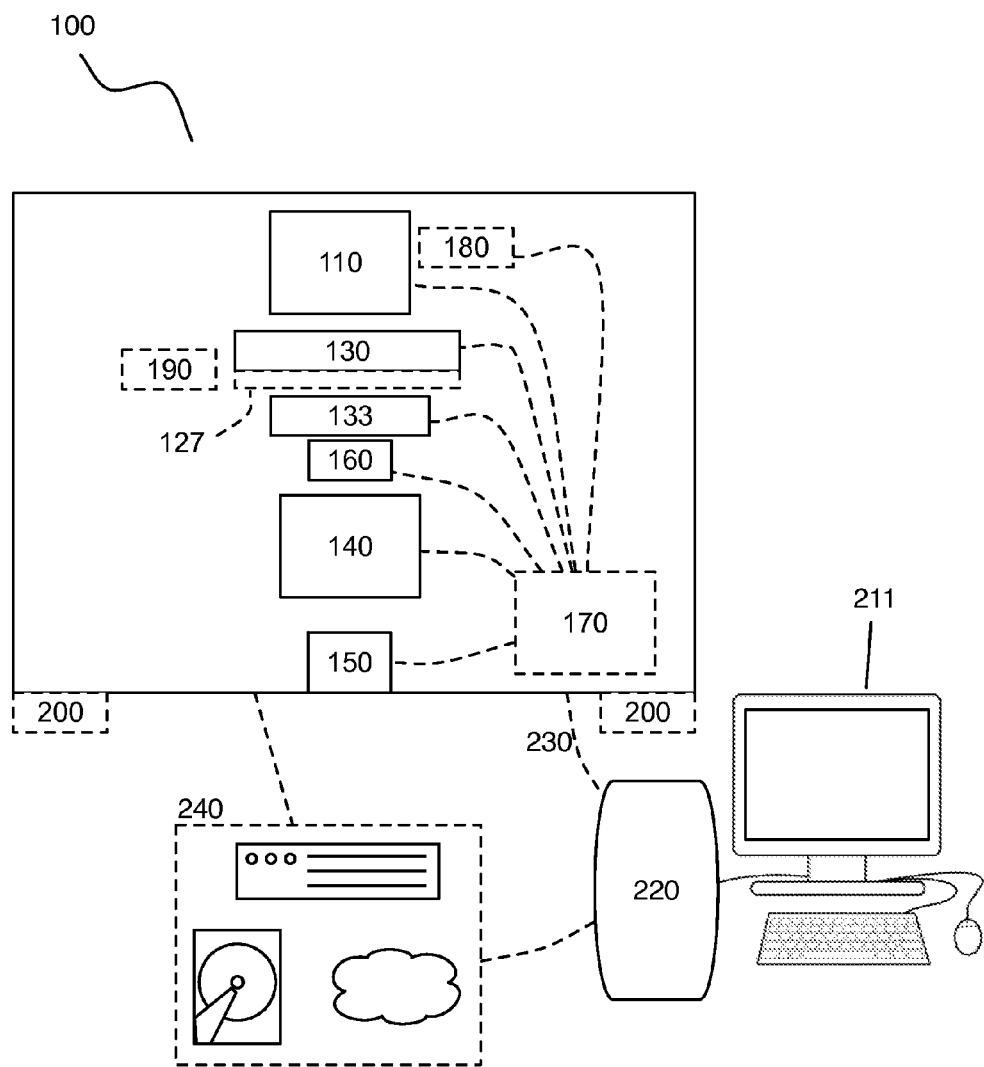
FIG. 1A depicts an embodiment of a system for imaging captured cells.

The following description of the preferred embodiments of the invention is not intended to limit the invention to these preferred embodiments, but rather to enable any person skilled in the art to make and use this invention.

1. System

As shown in FIGS. 1A-1D, an embodiment of a system 100 for detecting features of a biological sample at an imaging substrate comprises: an illumination module 110 configured to illuminate a target object (e.g., captured cells of interest within a microfluidic cell capture device) of the biological sample; a platform 130 configured to position the target object in relation to the illumination module 110; a filter module 140 configured to filter light transmitted to the target object and/or to filter light received from the target object; an optical sensor 150 configured to receive light from the target object and to generate image data; and a focusing and optics module 160 configured to manipulate light transmitted to the optical sensor 150. The system 100 can further comprise a control system 170 configured to control at least one of the illumination module 110, the platform 130, the focusing and optics module 160, the filter module 140, and the optical sensor 150; a tag identifying system 180 configured to identify and communicate tag information from system 100 elements; a thermal control module 190 configured to adjust temperature parameters of the system 100; an image stabilization module 200; a processor 220 configured to process information captured from the target object; and a linking interface 230 configured to transmit information between the processor 220, the optical sensor 150, the control system 170, and/or the thermal control module 190. The system 100 functions to facilitate manipulation and imaging of biological samples comprising captured cells of interest, in order to enable analyses of captured cells. The system 100 is preferably configured to receive a microfluidic cell capture device, such as the device described in U.S. application Ser. No. 13/557,510, entitled "Cell Capture System and Method of Use" and/or the device described in U.S. application Ser. No. 14/163,153, entitled "System and Method for Capturing and Analyzing Cells", which are both incorporated in their entirety herein by this reference. The system 100 can additionally accept other imaging substrates 350, such as microscope slides, tissue processing slides, microarray slides, tissue microarray slides, cell culture plates, and/or any other suitable imaging substrates 350. The system 100 can be capable of providing auto-focusing before image capture, but can alternatively take a series of images at multiple focal lengths, use image post-processing to sharpen the image, or utilize any other suitable method to achieve a focused image of a biological sample.

In a specific embodiment, the system 100 is configured to image captured cells within a microfluidic cell capture device that captures and isolates single cells of interest. In the specific embodiment, the system 100 provides unbroken, focused images of all microfluidic cell capture chambers in the microfluidic cell capture device, couples image data with target cell/device identifying information (e.g., location, time) and system parameter information (e.g., illumination information, temperature information), and facilitates light-based cellular diagnostic assays including assays involving fluorescent dyes (e.g., Hoechst dye, Alex Fluor 633, Hex, Rox, Cy5, and Cy5.5). The specific embodiment is further configured to be a benchtop system that operates below a specified decibel level, and is configured to not require room external room darkening to facilitate analyses of captured cells and/or other biological samples. Other variations can involve any other suitable configuration and/or combination of elements that enables imaging of captured cells, and can include elements described in U.S. application Ser. No. 13/557,510, entitled "Cell Capture System and Method of Use".

1.1 System—Illumination Module

The illumination module 110 comprises a first illumination subsystem in, and functions to transmit light toward one or more target objects (e.g., captured cells of interest) at the platform 130 to facilitate analyses of the target object(s). Preferably, the illumination module 110 comprises a first illumination subsystem in and a second illumination subsystem 121, such that multiple types of light-based analyses can be enabled by the system 100. The illumination module 110 can, however, comprise a single illumination subsystem or more than two illumination subsystems to facilitate multiple types of light-based analyses. Additionally, the illumination module 110 can comprise elements (e.g., housings, filters) configured to reduce or eliminate light not originating from the illumination module 110 (e.g., light within a room containing the system).

In a first variation, the first illumination subsystem 111 is a bright-field subsystem in and the second illumination subsystem is a fluorescence subsystem 121. The bright-field subsystem in preferably comprises a wide-spectrum light source as a first light source 112 (e.g., white light source) with an adjustable intensity, and is configured to transmit light through a first set of optics 113 toward a platform 130 configured to position captured cells. In other variations, the first light source 112 may not comprise a wide-spectrum of wavelengths, and/or may not be configured with an adjustable intensity. In one variation, the first light source 112 comprises a white light emitting diode (LED); however, the first light source 112 can additionally or alternatively comprise any other light source configured to provide bright-field images. Light from the first light source 112 thus illuminates a sample at an imaging substrate 350 at the platform 130, and contrast is provided by differential absorbance of light within the sample. The bright-field subsystem in preferably provides true bright-field images, but can additionally or alternatively provide composite bright-field images. The first set of optics 113 can comprise a collimator, which functions to collimate light from the first light source 112, and/or a focusing lens, which functions to focus light from the light source onto a captured cell. The focusing lens can be configured to focus light onto a single object (e.g., captured cell), or can one of a set of focusing lenses configured to focus light onto multiple objects (e.g., captured cells, region of a tissue sample) simultaneously. In a first variation, the first light source 112 and the first set of optics 113 are aligned in a vertical direction with respect to a horizontal platform 130, such that light is transmitted in a substantially perpendicular direction toward captured cells of interest at the horizontal platform 130. As such, in the first variation, the first light source 112 can be situated inferior to or superior to the platform 130. In an example of the first variation, light from the bright-field subsystem 111 is configured to impinge upon a biological sample comprising cells of interest, wherein the light is transmitted in a direction toward an optical sensor 150 located above (e.g., superior to) the biological sample, in the orientation shown in FIGS. 1B-1D. In another example of the first variation, light from the bright-field subsystem 111 is configured to impinge upon a biological sample comprising cells of interest, wherein the light is transmitted in a direction toward an optical sensor 150 located under (e.g., inferior to) the biological sample, in the orientation shown in FIG. 2A. In this example, the bright-field subsystem 111 is further configured to provide consistent illumination in two directions (e.g., in X and Y directions in a two-dimensional plane). However, the first light source 112 and the first set of optics 113 can alternatively be configured in any appropriate orientation and configured to direct light (e.g., using a mirror 102) to illuminate captured cells of interest with any suitable illumination profile. In other variations, the bright-field subsystem 111 can only comprise the first light source 112 and omit the first set of optics 113, or can comprise a first set of optics 113 including alternative or additional elements (e.g., mirror, lens, beam shaper, beam splitter).

In the first variation, the second illumination subsystem 121 is a fluorescence subsystem 121 comprising a wide-spectrum light source as a second light source 122 with an adjustable intensity, preferably including ultraviolet and/or infrared wavelengths of light, and a second set of optics 123 configured to manipulate light from the second light source 122. The fluorescence subsystem 121 may, however, not be configured to provide an adjustable intensity. In an example, the wide-spectrum second light source 122 comprises an LED that provides light with wavelengths at least in the range between 350-830 nm, such that the filter module 140 can filter light from the second light source 122 to appropriately enable fluorescence light-based analyses using fluorescent dyes (e.g., Hoechst dye, Alexa Fluor 633, FAM, Hex, Rox, Cy5, Cy5.5). However, the second light source 122 can additionally or alternatively comprise any other light source(s) configured to facilitate fluorescence light-based analyses. Additionally, the second light source 122 can comprise multiple light sources (e.g., multiple LEDs). In one example comprising multiple light sources, the multiple light sources can produce a certain range of light wavelengths, such that light from the multiple light sources can be filtered to reduced wavelength ranges for imaging and analysis of target objects according to specific assay protocols. The second set of optics 123 can comprise a collimator, which functions to collimate light from the second light source 122, and/or a focusing lens, which functions to focus light from the light source onto a captured cell. The focusing lens can be configured to focus light onto a single target object (e.g., captured cell), or can be one of a set of focusing lenses configured to focus light onto multiple target objects (e.g., captured cells, region of a tissue sample) simultaneously. In a first variation, the second light source 122 and the second set of optics 123 are aligned in a horizontal direction with respect to a horizontal platform 130, such that light is transmitted in a substantially parallel direction prior to being reflected (e.g., using a mirror 102) toward captured cells of interest or tissue at the horizontal platform 130. In an example of the first variation, light from the second illumination subsystem 121 is configured to impinge upon a biological sample comprising cells of interest, wherein the light from the second illumination subsystem 121 is transmitted in a direction away from an optical sensor 150 located above the biological sample, after being reflected by a mirror 102 and a dichroic mirror 143, in the orientation shown in FIGS. 1B-1C. In another example of the first variation, light from the fluorescence subsystem 121 is configured to impinge upon a biological sample comprising cells of interest, wherein the light is transmitted in a direction away from an optical sensor 150 located under the biological sample, in the orientation shown in FIG. 2A. However, the second light source 122 and the second set of optics 123 can alternatively be configured in any appropriate orientation to illuminate captured cells of interest with any suitable illumination profile. In other variations, the fluorescence subsystem 121 can only comprise the second light source 122 and omit the second set of optics 123, or can comprise a second set of optics 123 including alternative or additional elements (e.g., mirror, lens, beam shaper, beam splitter).

In alternative variations, at least one of the first illumination subsystem 111 and the second illumination subsystem 121 can comprise a dark-field subsystem, a confocal subsystem, a phase-contrast subsystem, and/or any other suitable imaging subsystem. Additionally, in other variations, at least one of the first illumination subsystem 111 and the second illumination subsystem 121 can be coupled to an actuation subsystem 128 configured to translate, rotate, or angularly displace a illumination subsystem 111, 121 relative to a biological sample comprising cells of interest.

1.2 System—Platform

Figure 1B:
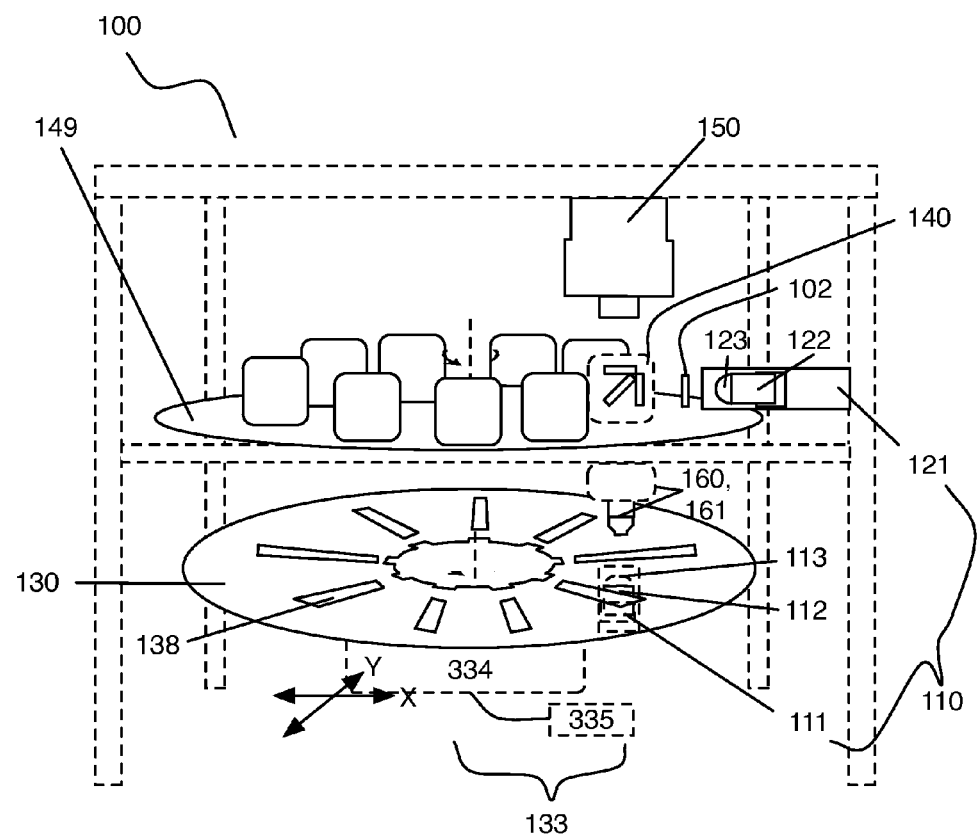
FIGS. 1B-1D depict portions of a variation of a system for imaging captured cells.
Figure 2A:
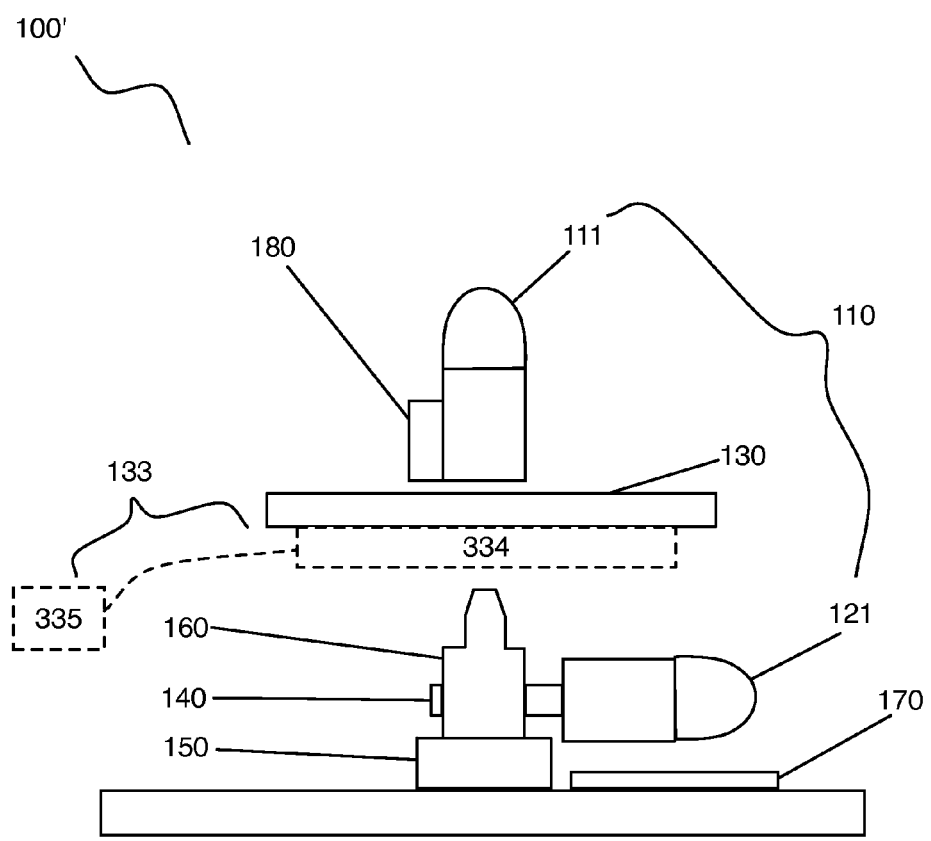
FIG. 2A depicts another variation of a system for imaging captured cells.

As shown in FIGS. 1A, 1B, and 2A, the platform 130 comprises a platform control module 133 and a guide 138, and can additionally or alternatively include an image normalizer 129. The platform 130 functions to receive and align a cell capture device or other imaging substrate 350 relative to the illumination module 110 and/or the optical sensor 150, in order to enable light-based analyses of captured cells of interest within the cell capture device or other imaging substrate 350. In some variations, the platform 130 can be automatically controlled by a control system 170, in order to facilitate automated functions including autofocusing of objects of interest, self-calibration, cell capture device interrogation, cell capture device agitation, or any other suitable function. In other variations, the platform 130 can be semi-automatically controlled or manually controlled, such that a user or other entity can manipulate the platform 130 in some manner (e.g., using knobs or dials mechanically coupled to the platform 130). Additionally, the platform 130 is preferably cleanable (e.g., using ethanol), such that the platform 130 can be reusable for multiple runs of analyses. The platform 130 is preferably situated between the first and the second illumination subsystems 111, 121, as described above, but can be located relative to any other suitable element of the system 100 in any other suitable manner.

As shown in FIGS. 1A, 1B, 2A, and 4B, the platform control module 133 functions to facilitate motion of the platform 130 relative to other elements of the system 100. The platform control module 133 preferably enables motion of the platform 130 in at least one direction, but can additionally be configured to enable motion of the platform 130 in two or three directions (e.g., X, Y, and/or Z directions). The platform control module 133 can additionally or alternatively provide rotational motion or any other suitable motion of the platform. To produce linear translations of the platform 130, a first variation of the platform control module 133 can comprise a translation stage 334 with a translation controller 335 (e.g., knobs that affect translation, actuator module that affects translation). The translation stage 334 in the first variation is also coupled to the platform 130 in order to enable translations of the platform 130 in X, Y, and/or Z directions. In an example of the first variation, as shown in FIGS. 5A-5C and 6, a first knob 134 with a flexible shaft extension can affect a translation of the platform 130 in the X direction, a second knob 135 with a flexible shaft extension can affect a translation of the platform 130 in the Y direction, and a third knob 136 with a flexible shaft extension can affect a translation of the platform 130 in the Z direction. Other variations of the platform control module 133 can comprise any other suitable element or subsystem (e.g., guiderails, springs, lead screws) configured to produce linear translations of the platform 130.

Figure 4A:
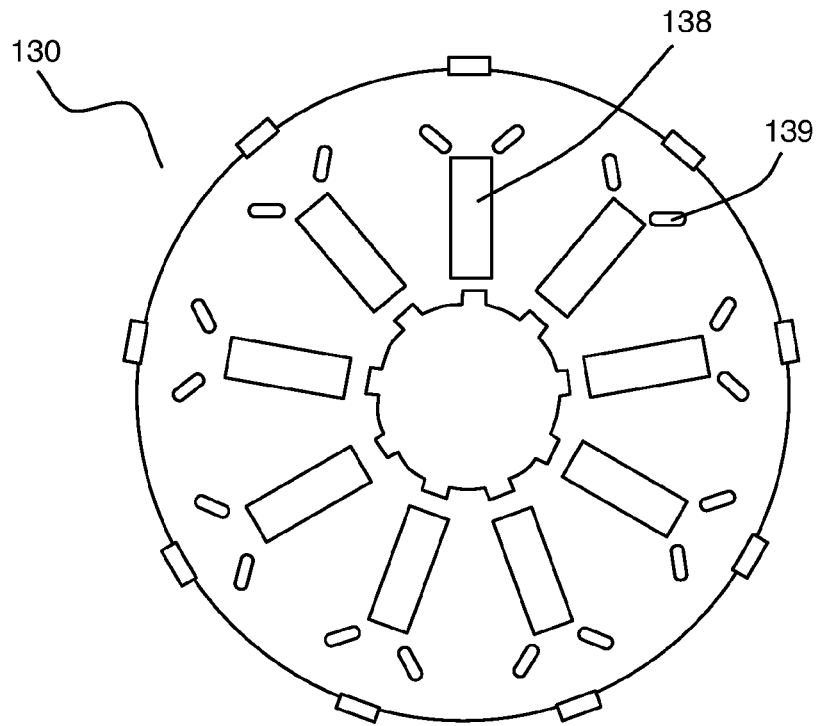
FIG. 4A depicts another example of a platform in an embodiment of a system for imaging captured cells.
Figure 4B:
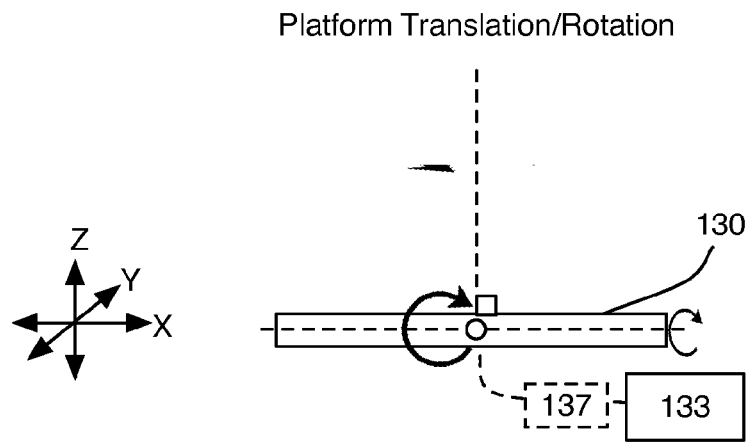
FIG. 4B depicts variations of manipulation of a platform of an embodiment of the system.
Figure 5A:
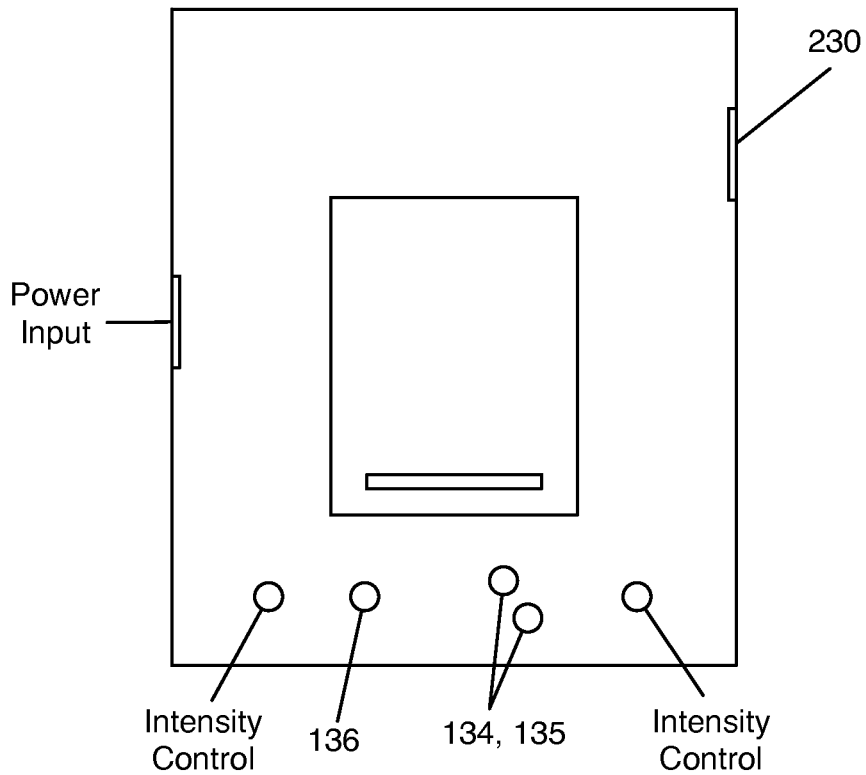
FIGS. 5A and 5B depict another embodiment of a system for imaging captured cells.
Figure 5B:
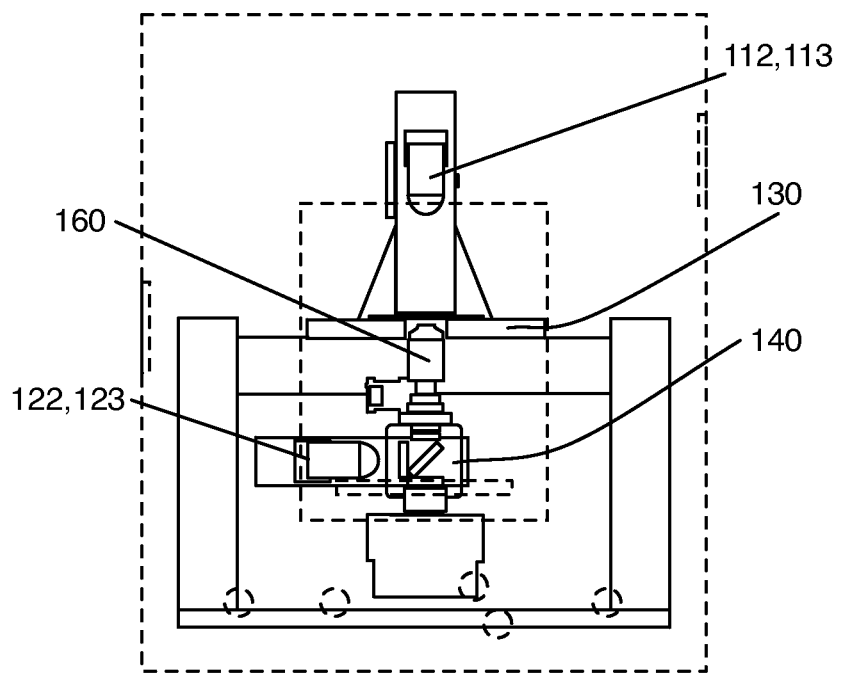
Figure 5C:
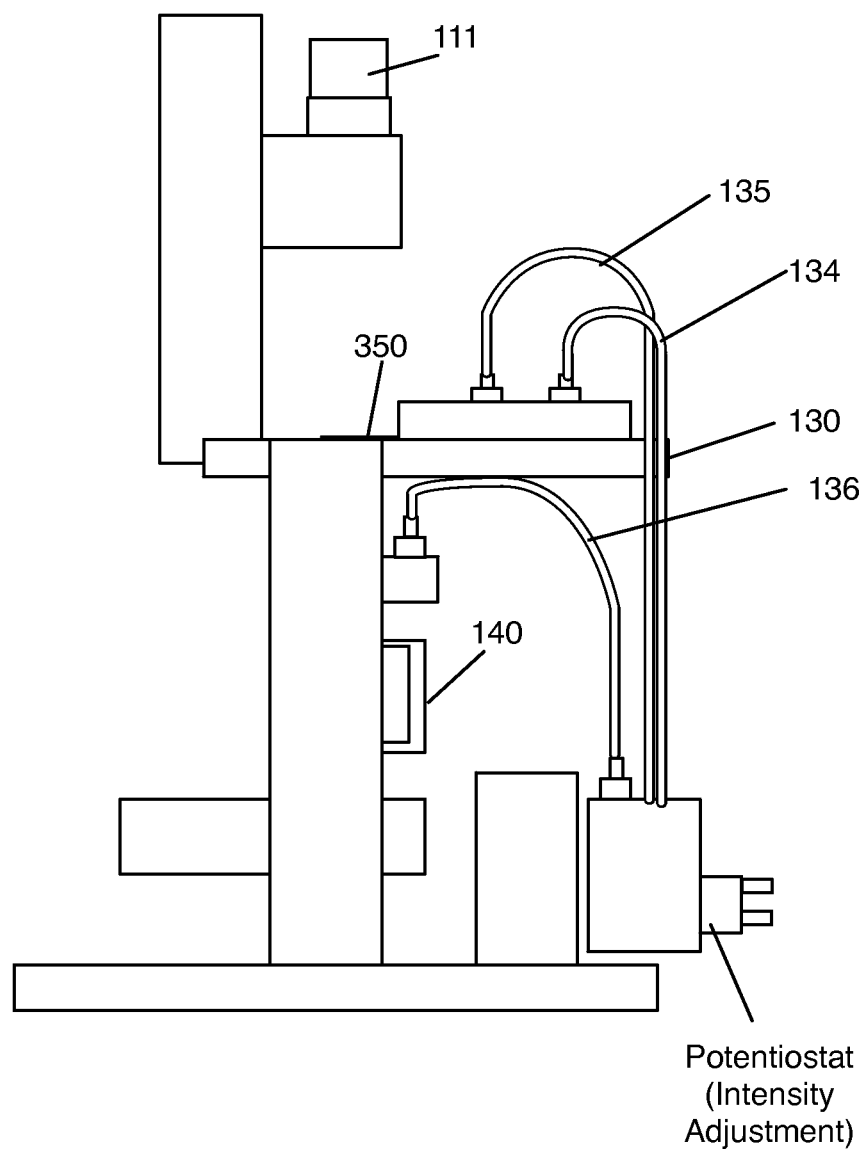
FIG. 5C depicts an example of a platform control module.
Figure 6:
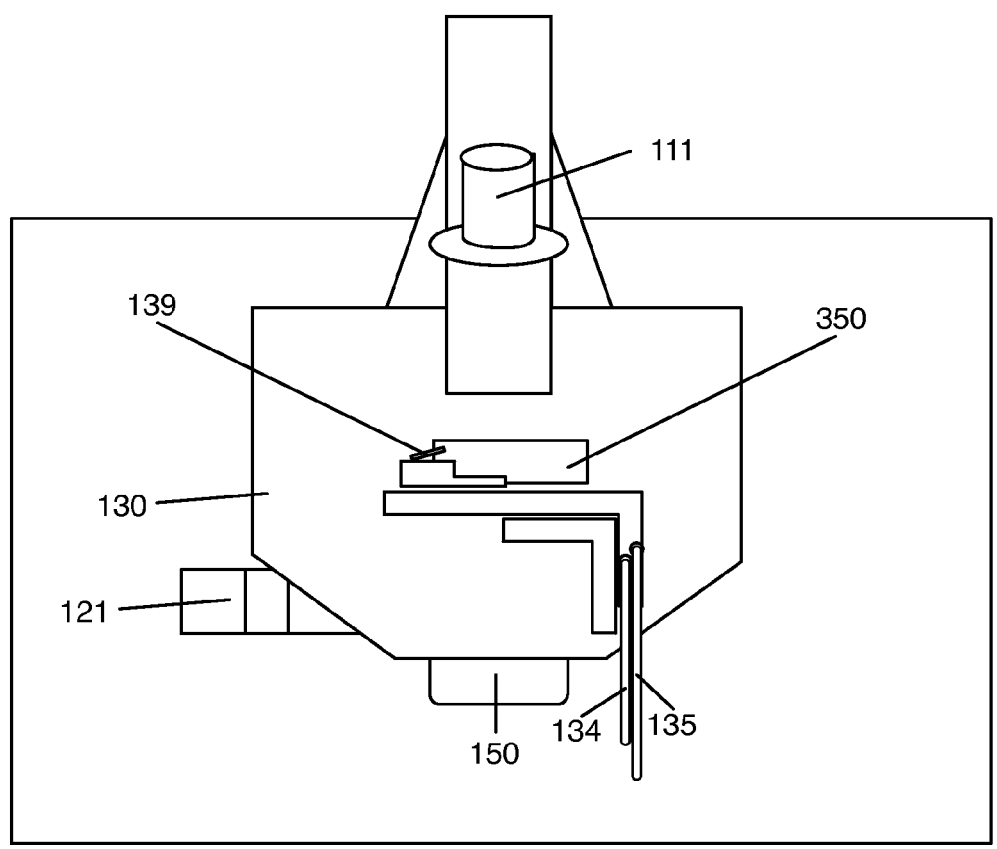
FIG. 6 depicts an example of a platform comprising a platform control module and a retainer.

As shown in FIG. 4B, the platform control module 133 can further be configured to angularly displace or rotate the platform 130, in order to provide images of target objects (e.g., captured cells of interest) in multiple orientations and/or to position target objects relative to other elements of the system 100. Angular displacement or rotation of the platform 130 can further facilitate auto-focusing and/or calibration functions of the system 100. As such, the platform control module 133 can be configured to angularly displace the platform about an axis parallel to the platform 130, about an axis perpendicular to the platform 130, and/or about an axis oriented in any other suitable manner relative to the platform. In an example, the platform control module 133 can be configured to angularly displace the platform 130 at a specified angle about an axis parallel to the platform 130, which results in a distribution of focal lengths across the platform (e.g., some platform locations will be in better focus than others based on the different resultant focal lengths). In the example, contrast differences generated from platform locations at different focal lengths are then interrogated by a processor 220 that determines the location with the greatest contrast, a measure indicative of the optimal focal length. The platform control module 133 in the example then angularly displaces the platform 130 to a horizontal configuration (e.g., a non-angularly displaced orientation), and translates the platform 130, to achieve the optimal focal length relative other system elements. In another example, the platform control module 133 displaces the platform about an axis perpendicular to the platform 130, such that different objects at the platform (e.g., imaging substrates 350) can be rotated into position and processed using the system 100.

In automated variations of the system 100, the platform control module 133 can comprise an actuator configured to automatically control motion of the platform 130. The actuator is preferably configured to affect motion of the platform 130 in at least two directions (e.g., X and Y directions); however, the actuator can be configured to affect motion of the platform 130 in less than two directions, more than two directions (e.g., X, Y, and Z directions), and/or in rotation. In an example of an automated variation, as shown in FIG. 1B, the platform control module 133 can comprise at least one motor coupled to a translation controller (e.g., of a translation stage 334), such that an actuation provided by the motor produces a translation of the platform 130. Specifically, the motor can be coupled to an X, Y, and/or Z translation stage controller 335 to produce motion of the platform 130. In another example, the platform control module 133 can comprise a stepper motor or any other suitable actuator, coupled to the platform 130, which enables rotation of the platform 130 and a rotational position of the platform 130 to be assessed. Other automated variations of the system 100 can comprise any suitable actuator coupled to any suitable platform translator or rotator to control motion of the platform 130.

Figure 3A:
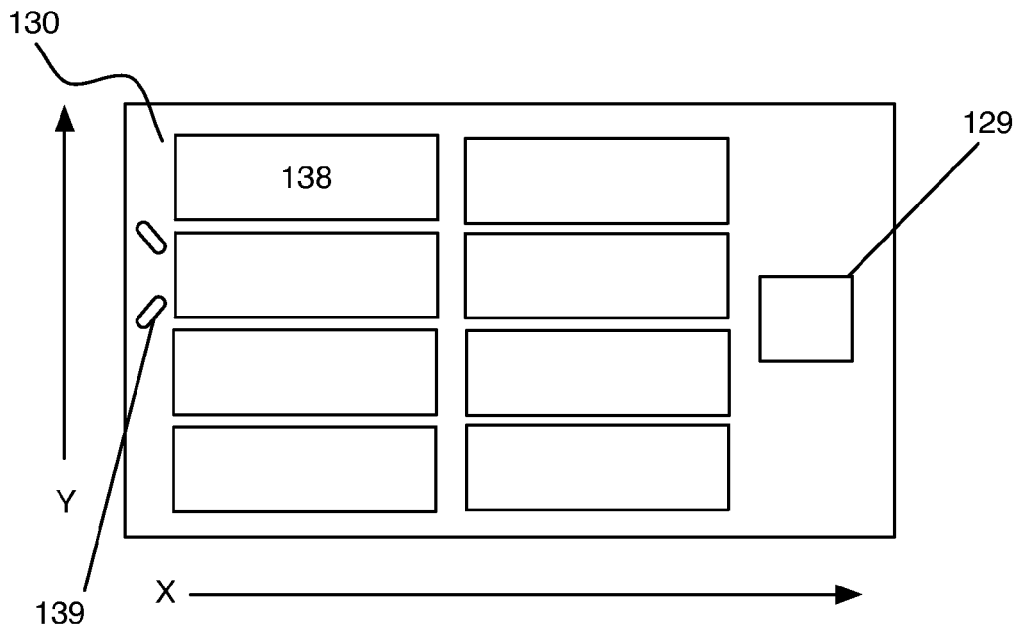
FIGS. 3A-3C depict examples of a platform comprising a guide and an image normalizer, an imaging substrate with a tag, and system calibration, respectfully.

The guide 138 functions to receive and align an imaging substrate 350 that contains a biological sample and/or target objects (e.g., captured cells of interest), such that the biological sample and/or target objects can be properly imaged and analyzed. The guide 138 can be a suitably-sized recess at one surface of the platform 130, and/or can comprise a ridge, rail, or tab configured to align the imaging substrate 350 in relation to the platform 130. Furthermore, the guide 138 can preferably only receive the imaging substrate 350 in one orientation, such that positive orientation confirmation is enabled by the guide 138; however, the guide 138 can alternatively be configured to receive an imaging substrate 350 in multiple orientations. The guide 138 preferably has at least one aperture in order to enable light transmission through the imaging substrate 350, thereby facilitating imaging of a target object at the imaging substrate 350. The guide 138 can additionally be one of a set of guides of the platform 130, such that the platform is configured to receive and align multiple imaging substrates 350. In one variation, the platform 130 can include an array of guides arranged in multiple rows, as shown in FIG. 3A, and in another variation, the platform 130 can include one or more guides 138 in a circular arrangement, as shown in FIG. 4A, such that a rotation of the platform 130 rotates successive imaging substrates 350, containing target objects (e.g., captured cells of interest), with respect to other elements of the system 100. Preferably, each guide 138 in the set of guides is identical; however, each guide 138 in the set of guides can alternatively be non-identical, such that different imaging substrates 350 (e.g., comprising different morphologies) can be received by the platform 130. Additionally or alternatively, the platform 130 can comprise a single guide 138 that is adjustable in order to accommodate differently sized imaging substrates 350.

As shown in FIGS. 3A and 4A, the guide 138 can further include a retainer 139 that holds the imaging substrate 350 at a specific location position relative to the rest of the platform 130. The retainer 139 is preferably capable of holding at least one imaging substrate 350 (e.g., cell capture device, glass slide, cartridge). In one variation, the retainer 139 can be a clip that biases the imaging substrate 350 against a brace, a recess in a surface of the platform 130, or any other suitable retainer 139. The platform 130 can be configured to accommodate one imaging substrate 350 at a time with a guide 138 and/or a retainer 139, as shown in FIG. 2B, but can alternatively be configured to accommodate multiple imaging substrates 350 simultaneously with multiple guides and/or multiple retainers, as shown in FIGS. 1B, 1C, 3A and 4A.

Figure 3B:
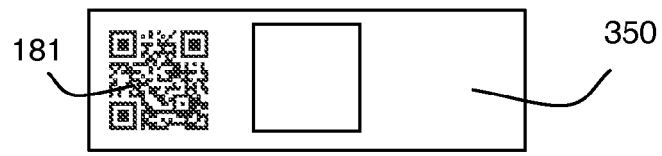
Figure 3C:
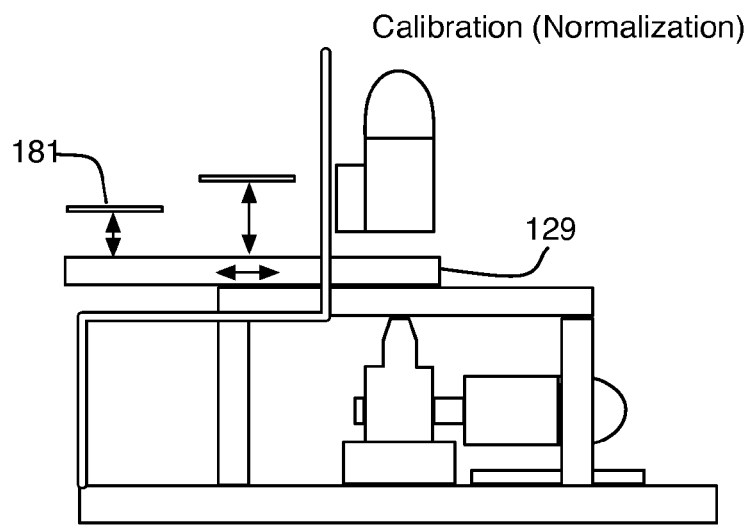

As shown in FIG. 3C, the image normalizer 129 is preferably coupled to the platform 130 and functions to facilitate calibration of the system 100. The image normalizer 129 preferably enables at least one of calibration of exposure and calibration of focus, but can additionally or alternatively enable calibration of other aspects of the system 100. Preferably, the image normalizer 129 is located within the same plane as the target object(s) intended to be imaged/analyzed by the system 100, such that a calibration using the image normalizer 129 can be adapted to facilitate imaging and/or analysis of the target object. The image normalizer 129 can additionally comprise a surface with features similar to those of target objects (e.g., captured cells of interest from a biological sample), to improve the suitability of the calibration. The image normalizer 129 can be in a fixed location relative to the platform 130, but can alternatively be configured to have an adjustable location relative to the platform 130. The image normalizer 129 can further enable automatic calibration of an aspect of the system 100 in automated variations of the system 100.

In other variations, the platform 130 additionally include or be coupled to a fluidic manifold 127 coupled to a fluid source, as shown in FIG. 1A, wherein the manifold 127 interfaces with an inlet and an outlet of a microfluidic cell capture device, such as the one described in U.S. application Ser. No. 13/557,510, entitled "Cell Capture System and Method of Use" or U.S. application Ser. No. 14/163,153, entitled "System and Method for Capturing and Analyzing Cells". The manifold 127 can thus enable visualization of real-time flow through the microfluidic cell capture device. In variations of the platform 130 configured to accommodate multiple imaging substrates 350, the manifold 127 can be configured to interface with inlets and outlets of multiple imaging substrates 350 (e.g., at openings of the manifold), in order to provide visualization of real-time flow through multiple cell capture devices; however, the manifold 127 can be configured in any other suitable manner.

In a first specific example, as shown in FIGS. 1B and 4A, the platform 130 comprises a guide 138 configured to receive and retain a microfluidic cell capture device or a glass slide with a 1"×3" footprint and a thickness between 1 mm and 2 mm. The guide 138 in the first specific example is one of a set of nine guides arranged in a circular array, as shown in FIG. 2D, such that the platform 130 accommodates up to nine microfluidic cell capture devices or other imaging substrates 350. In the first specific example, the platform 130 is rotatable (with a platform control module 133) about an axis perpendicular to the platform 130 through an angular displacement of at least 180° in clockwise and counterclockwise directions; however, in variations of the first specific example, the platform 130 can be rotatable through any other suitable angular displacement (e.g., 360° in one or two directions, less than 360° in one direction, etc.). In the first specific example, the platform control module 133 can additionally translate the platform in an X direction by a span of 9" and in a Y direction by a span of 5", using a multi-axis (e.g., X-Y) actuation system and a set of guide rails coupled to the platform. Thus, the first specific example allows each of up to nine microfluidic cell capture device(s)/glass slide(s) to be individually imaged and analyzed by the first specific example of the system 100. In other variations, the platform 130 can, however, comprise any suitable combination of elements and/or variations described to facilitate reception and alignment of an imaging substrate 350 relative to the illumination module 110 and/or the optical sensor 150.

In a second specific example, as shown in FIGS. 2B and 3A, the platform 130 comprises a guide 138 configured to receive and retain a microfluidic cell capture device or a glass slide with a 1"×3" footprint and a thickness between 1 mm and 2 mm. The guide 138 in the second specific example is one of a set of guides arranged in a 2×4 array, as shown in FIG. 2A, such that the platform 130 accommodates up to eight microfluidic cell capture devices or glass slides. In the second specific example, the platform 130 has a footprint of 9"×5" and is translatable (with a platform control module) in an X direction by a span of 9" and in a Y direction by a span of 5". Thus, the second specific example allows each of up to eight microfluidic cell capture device(s)/glass slide(s) to be individually imaged and analyzed by the second specific example of the system 100. In other variations, the platform 130 can, however, comprise any suitable combination of elements and/ or variations described to facilitate reception and alignment of an imaging substrate 350 relative to the illumination module 110 and/or the optical sensor 150.

1.3 System—Filter Module

The filter module 140 comprises an excitation filter 141 configured to receive light from a fluorescence subsystem 121 and transmit light at excitation wavelengths, a dichroic mirror 142 configured to receive and reflect light from the excitation filter 141 toward target objects at the platform 130, and an emission filter 143 configured to receive and transmit light from the target objects toward an optical sensor 150. The filter module 140 thus functions to transmit light at excitation wavelengths toward target objects (e.g., captured cells of interest) and to receive light at emission wavelengths from the target objects, in order to facilitate imaging and analysis of the target objects. The filter module 140 is preferably one of a set of filter modules of the system 100, however, the system 100 can alternatively include only a single filter module. The filter module(s) 140 can comprise a set of excitation filters 144, a set of emission filters 145, and a set of dichroic mirrors 146, such that multiple ranges of excitation light can be transmitted, and multiple ranges of emitted light can be transmitted to the optical sensor 150. In variations comprising a set of excitation filters 141, the set of excitation filters 141 can include band pass filters configured to transmit light between two bounding wavelengths, short pass filters configured to transmit light below a certain wavelength, and long pass filters configured to transmit light above a certain wavelength. Additionally, the set of excitation filters 141 can comprise interchangeable filters, such that individual excitation filters can be interchanged to provide different excitation wavelengths of light, and multiple excitation filters can be stacked to provide composite analyses; however, the set of excitation filters 141 can alternatively be fixed, such that the filter module 140 is only configured to transmit a fixed range of excitation wavelengths.

In a first variation comprising a set of excitation filters 144, excitation filters 141 in the set of excitation filters 144 are chosen to transmit different desired ranges of excitation wavelengths. In a first example of the first variation, the set of excitation filters 144 can comprise a filter that transmits light at wavelengths from 350-390 nm (for Hoescht dye-based assays), a filter that transmits light at wavelengths from 420-480 nm (for other Hoescht dye-based assays), a filter that transmits light at a nominal wavelength of 632 nm (for Alexa Fluor 633-based assays), and a filter that transmits light at a nominal wavelength of 647 nm (for other Alexa Fluor 633-based assays). In a second example of the first variation, the set of excitation filters 144 can comprise a filter that transmits light at wavelengths from 450-490 nm (for FAM-based assays), a filter that transmits light at wavelengths from 510-540 nm (for Hex-based assays), a filter that transmits light at wavelengths from 555-600 nm (for Rox-based assays), a filter that transmits light at wavelengths from 615-635 nm (for Cy5-based assays), and a filter that transmits light at wavelengths for 665-685 nm (for Cy5.5-based assays).

The dichroic mirror 142 of the filter module 140 is configured to align with an excitation filter 141, and functions to receive and reflect light from the excitation filter 141 toward a target object at the platform 130. The dichroic mirror 142 also functions to receive and transmit light from an emission filter 143 toward an optical sensor 150, which is described in more detail below. In variations comprising a set of dichroic mirrors 145, each dichroic mirror 142 in the set of dichroic mirrors 145 is preferably identical in orientation relative to an excitation filter 141 or a set of excitation filters 144, and an emission filter 143 of a set of emission filters 146. The dichroic mirror 142 or the set of dichroic mirrors 145 can also be configured to reflect and transmit appropriate wavelengths of light based on the application.

The emission filter 143 is configured to align with a dichroic mirror 142, and functions to transmit emission wavelengths of light from the target object at the platform 130, and to filter out excitation wavelengths of light. The filter module 140 can further comprise a set of emission filters 146, such that multiple different ranges of light wavelengths can be detected from the target objects at the platform 130. In variations comprising a set of emission filters 146, the set of emission filters 143 can include band pass filters, configured to transmit light between two bounding wavelengths, short pass filters configured to transmit light below a certain wavelength, and long pass filters configured to transmit light above a certain wavelength. Preferably, the set of emission filters 146 is interchangeable and/or stackable, such that individual emission filters can be interchanged or stacked to transmit and/or block different wavelengths of light; however, the set of emission filters 146 can alternatively be fixed, such that the filter module 140 is only configured to transmit a fixed range of emission wavelengths.

In a first variation comprising a set of emission filters 146, emission filters 143 in the set of emission filters 146 are chosen to transmit different desired ranges of emission wavelengths. In an example of the first variation, the set of emission filters 146 can comprise a filter that transmits light at wavelengths from 507-540 nm (for FAM-based assays), a filter that transmits light at wavelengths from 557-580 nm (for Hex-based assays), a filter that transmits light at wavelengths from 618-638 nm (for Rox-based assays), a filter that transmits light at wavelengths from 655-680 nm (for Cy5-based assays), and a filter that transmits light at wavelengths from 700-830 nm (for Cy5.5-based assays).

The filter module 140 can be fixed within the system 100, but can alternatively be coupled to an actuator configured to displace and/or align the filter module 140 relative to other system elements. As such, the filter module 140 can be coupled to a filter stage 149 coupled to the actuator and configured to translate and/or rotate the filter module 140 into position with respect to one or more light sources 112, 122 of illumination subsystems 111, 121 of the illumination module 110. Furthermore, the filter module 140 can be one of a set of filter modules coupled to a filter stage 149, such that each filter module 140 in the set of filter modules 140 can be translated or rotated into position with respect to one or more light sources 112, 122 of illumination subsystems 111, 121 of the illumination module 110. As such, the filter stage 149 preferably includes at least one aperture configured to allow light to be transmitted through the filter module(s) 140 to a target object at the platform 130; however, the filter stage 149 can additionally or alternatively be substantially transparent to allow light transmission, or can allow light transmission in any other suitable manner. Additionally, the filter stage 149 can be defined by a circular footprint, a rectangular footprint, or any other suitable footprint (e.g., polygonal, non-polygonal). The filter stage 149 is preferably situated superior to the platform 130 and inferior to an optical sensor 150; however, the filter stage 149 can alternatively be situated relative to other elements of the system 100 in any other suitable manner.

In one variation, the filter stage 149 can be coupled to an actuator that translates the filter stage 149 and the filter module(s) 140 along one or more axes (e.g., X, Y, and/or Z axes) into a desired position in a consistent manner (e.g., using a linear encoder, using a sensor able to provide position detection, etc.). In an another variation, the filter stage 149 can be coupled to an actuator that rotates the filter stage 149 and the filter module(s) 140 into a desired position in a consistent manner (e.g., using a rotary encoder, using a stepper motor, etc.), about an axis perpendicular to a planar surface of the filter stage 149. In this variation, the filter stage 149 is preferably rotatable by at least 180° in clockwise and counterclockwise directions; however, in variations of this variation, the filter stage 149 can be rotatable through any other suitable angular displacement (e.g., 360° in one or two directions, less than 360° in one direction, etc.). The axis of rotation of the filter stage 149 is preferably offset and parallel to the axis of rotation of the platform 130 in variations of the system 100 including a rotating platform 130; however, the axis of rotation of the filter stage 149 can alternatively be non-offset and/or non-parallel to the axis of rotation of the platform 130 in variations of the system 100 including a rotating platform 130. In still another variation, the filter stage 149 can be coupled to one or more actuators that translate the filter stage 149 and the filter module(s) 140 along one or more axes (e.g., X, Y, and/or Z axes) and rotate the filter stage 149 and the filter module(s) 140 into a desired configuration. In an example, as shown in FIG. 1A, the filter module 140 is one of nine filter modules coupled to a filter stage 149 defining a substantially circular geometry, with apertures defined within the filter stage 149 to allow light transmission through the apertures. In the example, each filter module 140 can be rotated into alignment with a second light source 122 of a second illumination subsystem 121 (e.g., a fluorescence subsystem), thereby allowing light from the second light source 122 to be transmitted through at least one excitation filter 141 of a filter module 140, and to be reflected at a 90° angle by a dichroic mirror 142 toward a target object at the platform 130, and allowing light from the target object to be transmitted through an emission filter 143 of the filter module 140 toward an optical sensor 150. As such, alignment of a filter module 140 in the example aligns the excitation filter 141 with the second light source 122, and simultaneously aligns the emission filter 143 with the optical sensor 150. However, in variations of the example, the filter module(s) 140 can be positioned into alignment with any other suitable elements of the system 100 in any other suitable manner.

In another specific example of the filter module 140, in the orientation shown in FIG. 2B, the filter module 140 comprises an excitation filter 141 oriented perpendicular to an emission filters 143, with a dichroic mirrors 142 bisecting an angle between two planes formed by the faces of the excitation filter 141 and the emission filter 143. In the specific example, light from the excitation filter 141 is thus substantially reflected at a 90° angle toward the platform 130, and light from the emission filter 143 passes in a substantially straight direction through the dichroic mirror 142 toward the optical sensor 150. Other variations of the filter module 140 can include any configuration of dichroic mirror(s), excitation filter(s), and/or emission filter(s) that enable transmission of light of excitation wavelengths toward a target object, and transmission of light from the target object toward an optical sensor 150.

1.4 System—Optical Sensor and Focusing and Optics Module

Figure 7A:
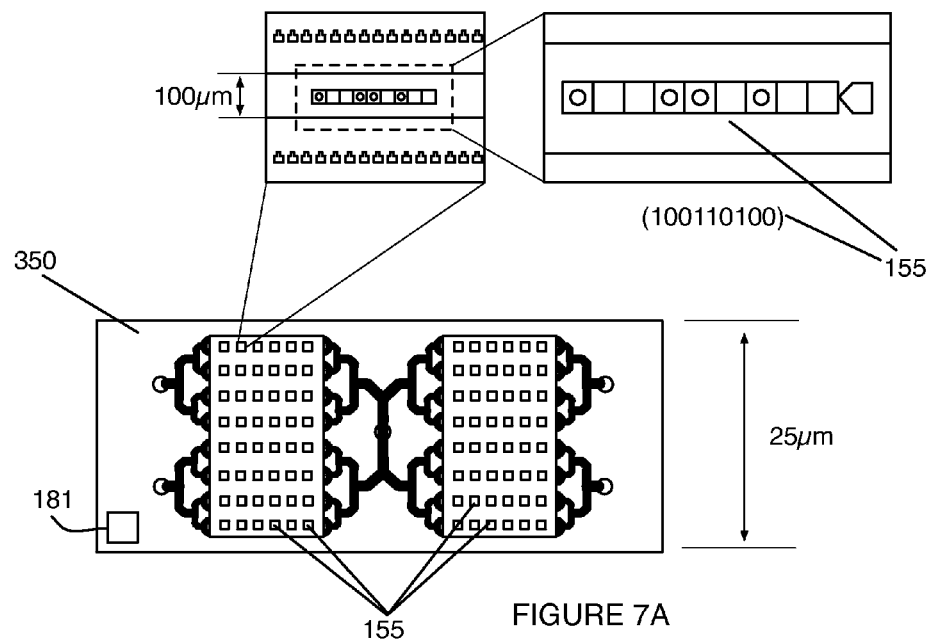
FIGS. 7A and 7B depict examples of cell capture device pore locations (e.g., zipcodes)
Figure 7B:
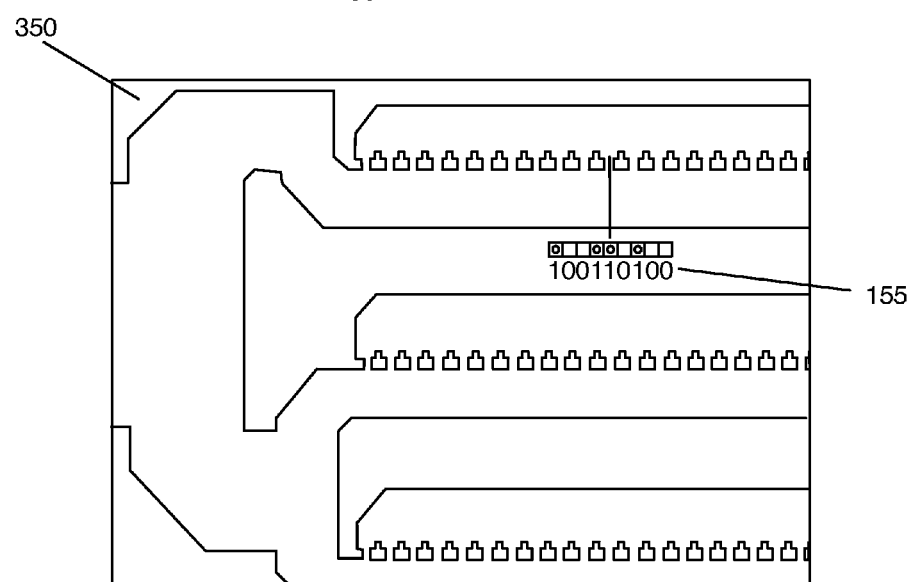

The optical sensor 150 is configured to align with an emission filter 143 of the filter module 140, and functions to receive light from the emission filter 143 to facilitate imaging and analysis of a target object (e.g., captured cell of interest). Preferably, the optical sensor 150 is oriented perpendicular to the platform 130, as shown in FIGS. 1B, 2A, and 2B, such that light from a target object at the platform 130 can be transmitted directly toward the optical sensor 150. In one variation, the optical sensor 150 is situated superior to the filter module 140 and the platform 130, and in another variation, the optical sensor is situated inferior to the platform. However, the optical sensor 150 can be oriented in any suitable configuration relative to the platform 130 and/or the filter module 140. The optical sensor 150 can comprise a photodiode comprising a photoelectric material configured to convert electromagnetic energy into electrical signals; however, the optical sensor 150 can alternatively comprise any other suitable appropriate photodetector for facilitating analysis of biological samples. The optical sensor 150 can comprise a charge-coupled device (CCD), a complementary metal-oxide-semiconductor (CMOS) sensor, a line scanner, or any other suitable imaging element. Additionally, the optical sensor 150 can facilitate imaging in color (e.g., red, green, blue, etc.). In an example, the system 100 comprising the optical sensor 150 can enable a 3-color analysis of a sample comprising captured cells of interest within 60 minutes. The optical sensor 150 can further provide image data in any suitable resolution (e.g., 1-10 pixels/micron, 5-100 megapixels) to distinguish between target objects and target object features, and can detect intensities of electromagnetic energy above a suitable threshold and between a certain range of wavelengths (e.g., 420-830 nm). In a specific example, the optical sensor 150 is configured to enable differentiation of a single cancer cell in a background of contaminating white blood cells by providing images of sufficient resolution and/or color imaging for fluorescent detection. In the specific example, as shown in FIGS. 7A and 7B, the optical sensor 150 can further provide a suitable resolution of image data, such that the system 100 can differentiate between specific cell capture pore locations 155 (e.g., addresses) of a microfluidic cell capture device, such as that described in U.S. application Ser. No. 13/557,510 or U.S. application Ser. No. 14/163,153. In the specific example shown in FIGS. 7A and 7B, the pore locations 155 are characterized by tags translatable to a binary number by a processor 220, and include a series of characters wherein a character with a dot indicates a value of "1" and a character without a dot indicates a value of "0". As such, in the specific example, each tag translatable to a binary number has a series of nine characters, each character having a dot or no dot that is detectable by the optical sensor 150 and/or a tag identifying system 180 as described in further detail below. In another variation of this specific example, a combination of dots can be used as a tag wherein a feature (e.g., relative distance, color, intensity, shape, etc.) between the dots indicate a precise location of the tag within the microfluidic device. In variations of the specific example, however, the pore locations 155 can be characterized by any other suitable tag (e.g., RFID tag, visually detectable tag, non-visually detectable tag, etc.) and be detectable by any other suitable method (e.g., RF sensing, visual detection, etc.).

The focusing and optics module 160 preferably comprises a lens 161 configured to focus light from the illumination module onto a target object at the platform 130, and/or a lens 162 configured to focus light from the target object at the platform 130 onto the optical sensor 150. The lens can be any suitable lens (objective lens) with any suitable magnification (e.g., 10×-40×) and numeric aperture (e.g., ¼"). The lens 161, 162 can also be one of a set of lenses configured to focus light onto individual target objects (e.g., individual lenses focus light onto individual captured cells of interest), or can be a single lens 161 configured to focus light onto multiple target objects (e.g., captured cells of interest within a microfluidic cell capture device, a tissue region, etc.) at the platform 130. The lens(es) 161, 162 can be aligned with the excitation filter 141, the dichroic mirror 142, and/or the emission filter 143 of the filter module 140, such that light transmitted from or reflected off of the excitation filter 141, the dichroic mirror 142, and/or the emission filter 143 is appropriately focused. The lens(s) can however, be aligned in any suitable configuration relative to other elements of the system 100 and configured to focus incident light by way of any suitable number of optics elements (e.g., dichroic mirrors, mirrors, etc.).

The lens(es) 161 of the focusing and optics module 160 can be further configured to translate in one or more directions and/or rotate about any suitable number of axes, to facilitate focusing or auto-focusing of light onto the platform 130 and/or onto the optical sensor 150. In variations wherein the lens(es) 161 of the focusing and optics module 160 are configured to translate, translation can be facilitated using an optics manipulation module 167, including an actuator 166 and/or a lens selector 165, to enable automated or semi-automated functionalities (e.g., autofocusing, automagnification, etc.). The actuator 166 preferably couples to the lens(es) 161, 162 and/or the lens selector 165, and provides translation along at least one axis (e.g., X-axis, Y-Axis, Z-axis); however, the actuator 166 can be configured to couple to any other suitable element of the system 100 in order to enable translation of elements of the focusing and optics module 160, and/or can provide translation along multiple axes (e.g., X and Z-axes, Y and Z-axes, X and Y-axes). The lens selector 165 preferably rotates one of a set of lenses into alignment (e.g., as in a revolving nosepiece); however, variations of the lens selector 165 can additionally or alternatively translate a lens of a set of lenses into alignment.

Figure 1C:
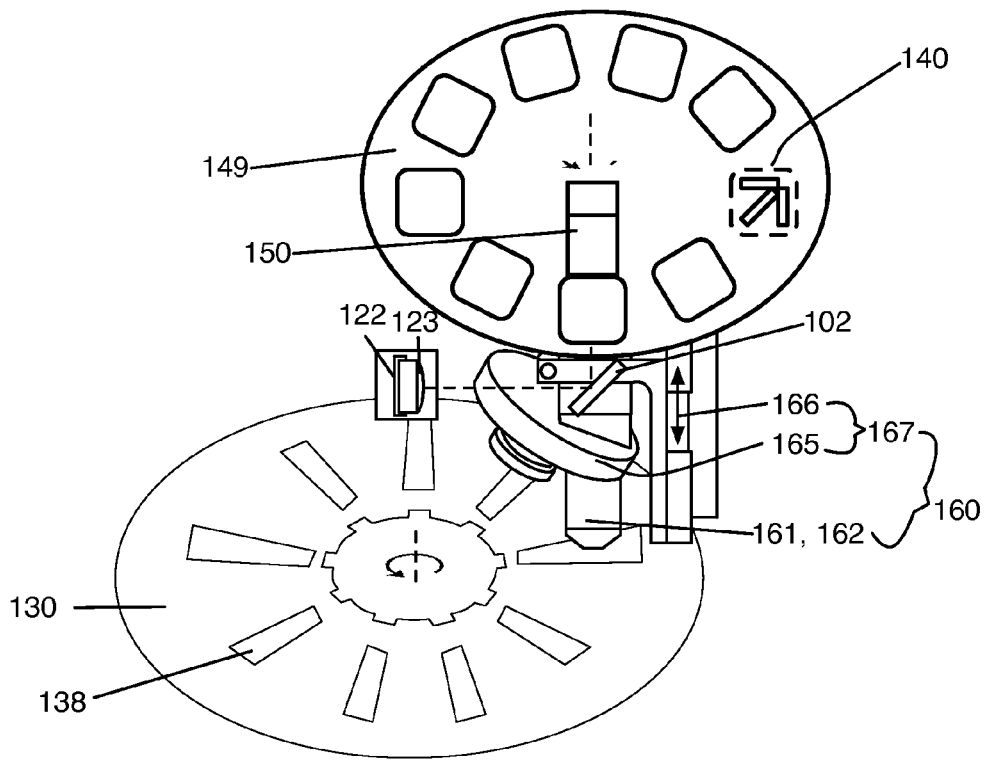
Figure 1D:
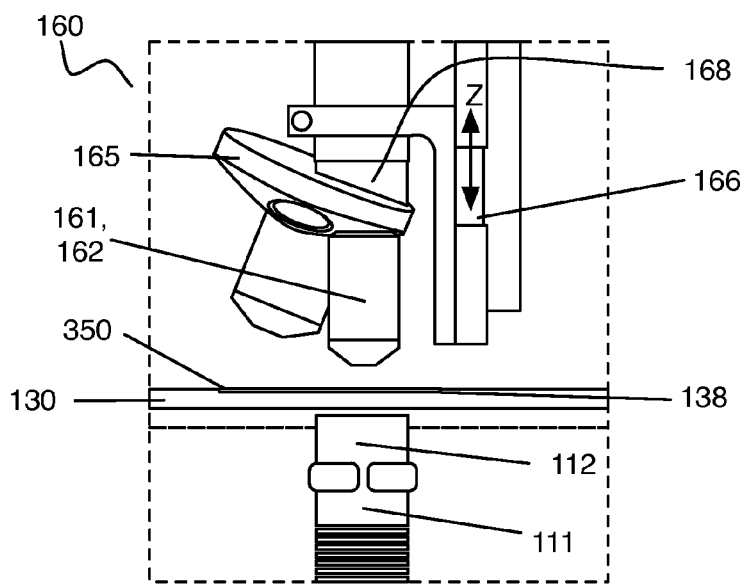
Figure 2B:
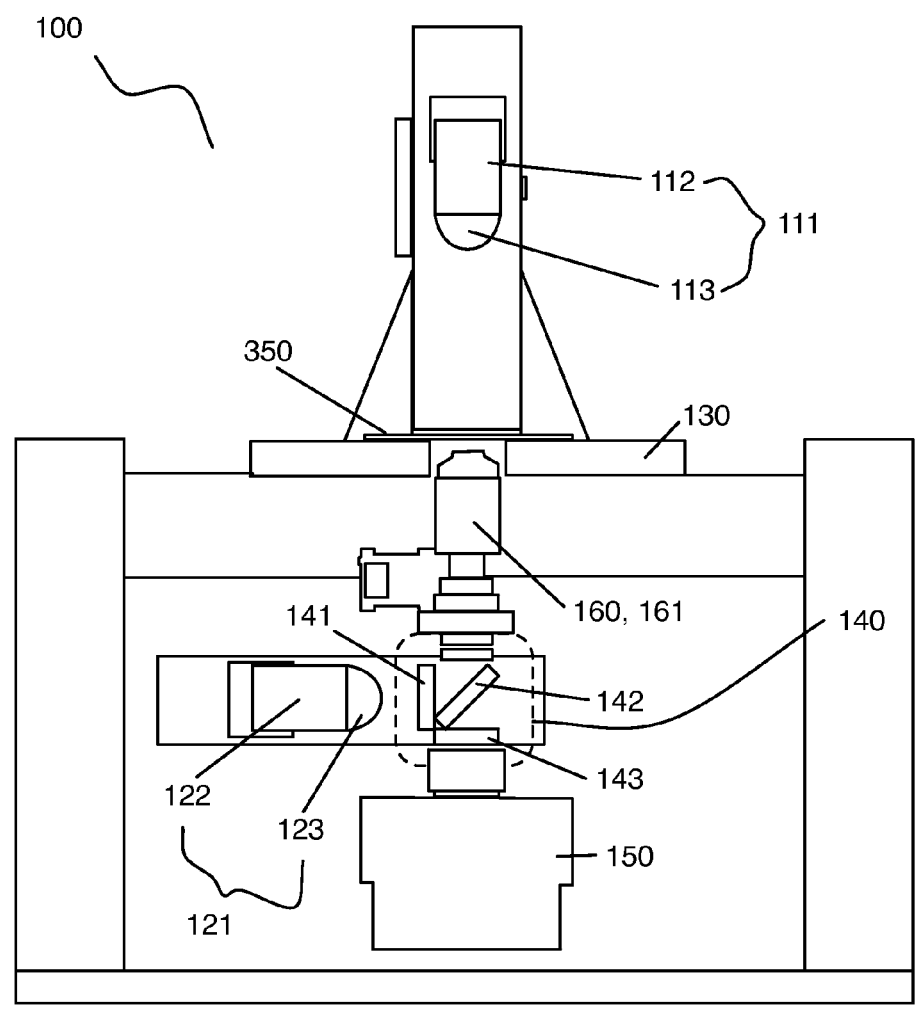
FIG. 2B depicts another variation of a system for imaging captured cells.

In a specific example, as shown in FIGS. 1C and 1D, the optics manipulation module 167 includes a revolving nosepiece as the lens selector 165, configured to reversibly couple to three objective lenses that can be rotated into alignment with a corresponding element of the system 100 (e.g., a filter module 140, a first illumination subsystem 111, a second illumination subsystem 121, etc.). The revolving nosepiece in the specific example rotates about an axis angularly displaced from a vertical axis, in the orientation shown in FIGS. 1C and 1D, such that an aligned lens is rotated into a vertical configuration, and a misaligned lens is rotated into a non-vertical configuration. In the specific example, the revolving nosepiece is coupled to a linear translation stage (e.g., ThorLabs MTS25/M-Z8 translation stage) as an actuator 166 configured to translate the lens selector 165 along a Z-axis, in the orientation shown in FIGS. 1C and 1D. In further detail, to provide translation along the Z-axis, an optical shaft 168 coupled to the revolving nosepiece and concentric with an aligned lens 161, 162 is coupled to the actuator 166 by an L-shaped plate (e.g., an L-bracket), thereby facilitating motion of the lens 161, 162 along a Z-direction. Variations of the specific example can, however, include an optical shaft 168 not aligned with a lens 161, 162 of the focusing and optics module 160, and/or can include coupling in any other suitable manner to affect translation of a lens 161, 162 along any suitable axis. In the specific example, the actuator 166 is coupled to a controller configured to provide autofocusing of the focusing and optics module 160; however, variations of the specific example can omit coupling between a controller and the actuator 166, and enable manual translation of the lens(es) 161, 162. Variations of the specific example can further allow rotation or translation of the lens(es) 161, 162 of the focusing and optics module 160 into any other suitable configuration, in any other suitable manner.

Furthermore, while variations and examples of translation and/or rotation in the platform 130, the filter module 140, and the focusing and optics module 160 have been described above, other embodiments of the system 100 can include translation, rotation, and/or relative motion through any suitable path, of any suitable element of the system 100, in order to facilitate light transmission and alignment of optics elements in any other suitable manner.

1.6 System—Other Elements

As shown in FIGS. 1A and 2A, the system 100 can further comprise a tag identifying system 180. The tag identifying system 180 functions to read barcodes, QR codes and/or any other identifying tags 181 of the system 100, and to communicate information from the identifying tags to a processor 220. The tag identifying system 180 can be coupled to the illumination module 110, as shown in FIG. 2A, to facilitate identification and reading of tags located on imaging substrates 350 coupled to the platform 130, or any other suitable system element. In other variations, the tag identifying system 180 may not be coupled to the illumination module 110.

The tag identifying system 180 is preferably fixed in location, but can alternatively be configured to move relative to other system elements. In one alternative variation, the tag identifying system 180 can be a standalone unit that is configured to be manipulated by a user to scan tags or labels located on elements of the system 100. The tag identifying system 180 can comprise a barcode reader, a radio-frequency identification (RFID) reader, a QR code reader, a nearfield communication device, or any other suitable element implementing a mechanism that can identify a unique identifier located on the an imaging substrate 350 or other aspect of the system 100 (e.g., glass slide, cartridge, cell capture device, etc.). The tag identifying system 180 can alternatively or additionally be configured to parse and interpret non-encoded information (e.g., text) on an identifying tag 181. In some variations of the system 100, the optical sensor 150 can additionally function as a tag identifying system 180.

As shown in FIG. 3B, a tag 181 intended to be identified and/or read by the tag identifying system 180 preferably communicates information to the tag identifying system 180 upon being read. The information can comprise information related to imaging substrate 350 (e.g., cell capture device, glass slide) identification information, protocol information (e.g., staining protocol information), information related to suggested system parameters required to actualize a protocol, information related to calibration of the system 100 with regard to a specific imaging substrate 350, information related to contents of an imaging substrate 350, information configured to facilitate positive location identification of an imaging substrate 350 or locations within an imaging substrate 350, and/or any other suitable type of information. The information can be coupled to (e.g., embedded within) image data captured by the optical sensor 150, and/or can be communicated to the processor 220 using any other suitable means.

As shown in FIGS. 1A and 7, the system 100 can further comprise a thermal control module 190, which functions to controllably heat and/or cool aspects of the system 100 to facilitate imaging and analysis of target objects (e.g., captured cells of interest). As such, the thermal control module 190 controls thermal parameters of at least one of the imaging substrate and a biological sample at the imaging substrate. The thermal control module 190 is preferably coupled to the platform 130, but can alternatively be at a location within proximity of the platform 130, or may not be within proximity of the platform 130. The thermal control module 190 can be configured to heat aspects of the system by conduction, convection, and/or radiation using a heating element. The thermal control module 190 can additionally or alternatively comprise a cooling element configured to cool or modulate heat within the system 100. Alternatively, cooling can be enabled by deactivating a heating element. The thermal control module 190 preferably includes electric heaters, but can alternatively include inductive heaters, ceramic heaters, or any other suitable heaters. The thermal control module 190 can additionally include a heat sink, heat pump, heat exchanger, fan, or any other suitable passive or active cooling mechanism. The thermal control module 190 is preferably optically transparent to facilitate unobstructed imaging, but can alternatively have any other suitable optical property such that imaging by the system 100 is not obstructed. In variations, the thermal control module 190 can be configured to move out of a field of view after heating and/or cooling a substrate, to enable unobstructed imaging.

In one variation, the thermal control module 190 comprises a single element configured to contact a surface of an imaging substrate 350. In another variation, the thermal control module includes multiple elements, wherein each element is configured to heat or cool a given portion of an imaging substrate 350. In one example, the thermal control module 190 can be used to control the temperature of a microfluidic cell capture device being imaged and/or analyzed by the system 100, by heating and/or cooling the microfluidic cell capture device according to a specific protocol during imaging. In an example, of the variation, the thermal control module 190 can heat the microfluidic cell capture device to incubate the cells of interest captured therein, and can cool microfluidic cell capture device to quench a reaction or incubation process.

Figure 8:
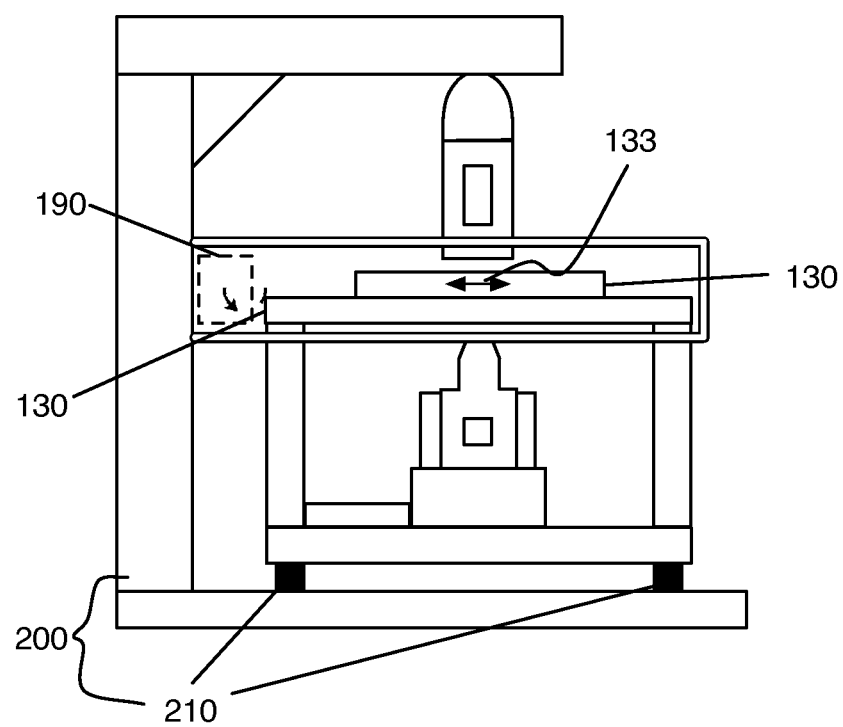
FIG. 8 depicts an example of a system comprising a thermal control module and an image stabilization module.

The system 100 can further comprise an image stabilization module 200 configured to reduce or eliminate artifacts within image data due to unwanted system 100 motion. In one variation, as shown in FIG. 8, the image stabilization module 200 can comprise vibration isolators 210 (e.g., feet, pads, platforms) configured to reduce or entirely eliminate system vibration. In another variation, the image stabilization module 200 can comprise image stabilization software, implemented on a processor 220 configured to receive image data from the optical sensor 150. The image stabilization software can be configured to anticipate and counteract system motion (e.g., by moving the platform 130, optical sensor 150, and/or focusing and optics module 160 in a compensatory manner). The image stabilization software can alternatively be configured to post-process image data comprising unwanted motion artifacts, in order to remove the unwanted motion artifacts. In other variations, the image stabilization module 200 can comprise any other suitable image stabilization device or method.

As shown in FIGS. 1A and 2A, the system 100 can further comprise a control system 170, which functions to control at least one of parameters of the illumination module 110 (e.g., intensity), motion of the platform 130, filter configurations of the filter module 140, imaging parameters of the optical sensor 150, identification and reading of tags 181 by the tag identifying system 180, temperature parameters provided by the thermal control module 190, and/or any other system function. Thus, the control system 170 can be electronically and/or physically coupled to the illumination module, the platform 130, the filter module 140, the optical sensor 150, the focusing and optics module 160, the tag identifying system 180, the thermal control module 190, and/or the image stabilization module 200. The control system 170 can enable fully-automated control of parameters of the system 100, or can facilitate semi-automated/manual control of parameters of the system 100.

In a variation wherein the control system 170 is coupled to the illumination module 110, the control system 170 can function to adjust light intensity provided by the illumination module 110. For example, the control system 170 can control bright field illumination intensity and fluorescence illumination intensity using potentiostats or other suitable elements. In a variation wherein the control system 170 is coupled to the platform 130, the control system 170 can function to manipulate translation, angular displacement, and/or rotation of the platform 130 about any suitable number of axes. In a variation wherein the control system 170 is coupled to the filter module 140, the control system 170 can facilitate adjustments to filter configurations (e.g., interchanging and/or stacking of fillers) to enable various light-based biological sample assays to be performed. In a variation wherein the control system 170 is coupled to the optical sensor 150, the control system 170 can adjust image capture parameters (e.g., resolution, capture, exposure, etc.). In a variation wherein the control system 170 is coupled to the focusing and optics module 160, the control system 170 can facilitate motion of the platform 130 and/or the focusing and optics module 160, in order to enable autofocusing functions of the system 100. For example, the system 100 can autofocus to depth fiducials of a cell capture device, or can autofocus on individual cells captured within a cell capture device. In a variation wherein the control system 170 is coupled to the tag identifying system 180, the control system 170 can function to automate reading of tags 181, and can further function to facilitate transfer of information from the tags 181 to a processor 220. In a variation wherein the control system 170 is coupled to a thermal control module 190, the control system 170 can facilitate heating of an imaging substrate 350 to a specified thermal state (e.g., temperature), maintaining the imaging substrate 350 at the specified thermal state, and/or cooling the imaging substrate 350. Other variations of the control system 170 can function automate handling, transfer, and/or storage of other elements of the system 100, Alternative combinations of the above variations can involve a single control element, or multiple control elements configured to perform all or a subset of the functions described above.

As shown in FIG. 1A, the system 100 can further comprise a processor 220, which functions to receive and process information from the optical sensor 150, the control system, a tag identifying system 180, and/or any other suitable system element. Preferably, the processor 220 implements image processing software configured to process image data from the optical sensor 150, and can be coupled to a user interface 211 with a display, as shown in FIG. 1A. In one such variation, the processor 220 can include a module configured to receive a dataset from the optical sensor 150 to calibrate at least one of the optical sensor 150 and the optics manipulation module 167, based upon a distribution of focal lengths between the optical sensor 150 and the platform 130 (e.g., based upon a focal length providing a maximum contrast level). In another variation, the processor 220 can include a module configured to facilitate analysis of real-time fluid flow at the at least one imaging substrate 350 based upon data generated by the optical sensor 150. In another variation, the processor 220 can include a module configured to translate a series of characters, physically defined at an imaging substrate 350 (e.g., proximal to a pore of the array of parallel pores) and detectable using the optical sensor 150, into a binary number indicative of an address (e.g., of the pore) characterized by the series of characters. The processor 220 can, however, include any other suitable modules configured to perform any other suitable function.

In variations comprising a user interface 211 with a display, the user interface 211 functions to display processed and/or unprocessed data produced by the system 100, settings of the system 100, information obtained from tag identifying system 180, or any other suitable information. Alternatively, the processor 220 may not be coupled to a user interface 211, and/or can comprise a linking interface 230 configured to facilitate transfer of processed and/or unprocessed data produced by the system 100, settings of the system 100, information obtained from a tag identifying system 180, or any other appropriate information to a device external to the system 100.

The linking interface 230 is preferably a wired connection, wherein the linking interface 230 is configured to couple to a wired connector. The linking interface 230 can facilitate one-way and or two-way communication between system elements and the processor, and can communicate with the processor via inter-integrated circuit communication (I2C), one-wire, master-slave, or any other suitable communication protocol. However, the linking interface 230 can transmit data in any other way and can include any other type of wired connection (such as a USB wired connection) that supports data transfer between system elements and the processor 220. Alternatively, the linking interface 230 can be a wireless interface. In a wireless variation of the linking interface 230, the linking interface 230 can include a Bluetooth module that interfaces with a second Bluetooth module coupled to another element over Bluetooth communications. The linking interface 230 of the wireless variation can alternatively implement other types of wireless communications, such as Wi-Fi, 3G, 4G, radio, or other forms of wireless communication.

Other elements of the system 100 can include a storage module 240, which functions to provide local system storage of data. Variations of the system 100 including a storage module thus allow data to be stored locally prior to transferring the data to an element external to the system. In a specific example, the storage module can provide local storage adequate to accommodate storage of up to 10 runs of the system 100 per day, for a month period of time.

1.7 System—Specific Examples

In a first specific example, as shown in FIGS. 1B-1D, the platform 130 is situated intermediately between the first illumination subsystem 111 comprising a bright-field subsystem and the second illumination subsystem 121 comprising a fluorescence subsystem, wherein the first light source 112 of the first illumination subsystem 111 is configured to transmit light through a first set of optics 113 directly toward an imaging substrate 350, at the platform 130, located superior to the first illumination subsystem 111. Light from the first light source 112 and transmitted through the imaging substrate 350 is then directed toward an optical sensor 150 at a location superior to the platform 130, through a filter module 140. Furthermore, the second light source 122 of the second illumination subsystem 121 is configured to transmit light toward a mirror 102 to be reflected at a 90° angle into a second set of optics 123 through at least one excitation filter 141 of the filter module 140, which reflects by a 90° angle at a dichroic mirror 142 of the filter module 140, through a focusing an optics module 160 and toward the imaging substrate 350 located inferior to the second illumination subsystem 121, at the platform 130. In the first specific example, light from at least one target object at the imaging substrate 350 is then configured to be transmitted through the focusing and optics module 160, directly through the dichroic mirror 142, and toward the optical sensor 150 situated superior to the filter module 140. In the first specific example, the filter module 140 is one of nine filter modules 140 coupled to a filter stage 149 defining a substantially circular geometry, with apertures defined within the filter stage 149 to allow light transmission through the apertures. The filter stage 149 defines a plane substantially parallel to a plane defined by the platform 130, and the filter stage 149 is located at a position superior to that of the platform 130. In the first specific example, each filter module 140 of the three filter modules can be rotated into alignment with the second light source 122 of the second illumination subsystem 121, thereby allowing light from the second light source 122 to be transmitted through at least one excitation filter 141 of a filter module 140 and to be reflected at a 90° angle by a dichroic mirror 142 toward a target object at the platform 130, and allowing light from the target object to be transmitted through an emission filter 143 of the filter module 140 toward the optical sensor 150 superior to the filter stage 149. As such, alignment of a filter module 140 in the first specific example aligns the excitation filter 141 with the second light source 122, and simultaneously aligns the emission filter 143 with the optical sensor 150.

In the first specific example, the platform 130 comprises nine guides 138 arranged in a uniformly distributed circular array, each guide 138 proximal to a retainer 139 that holds an imaging substrate 350 at the platform 130. The platform 130 in the first specific example is further coupled to a platform control module 133 comprising a translation stage 334 configured to translate the platform 130 in coordinate directions parallel to the platform 130 (e.g., X, Y directions), by way of a translation controller 335 that automates translation of the translation stage 334. The platform control module 133 in the second specific example further includes an actuator configured to angularly displace the platform 130 about an axis perpendicular to the platform, thereby rotating one of multiple imaging substrates 350 with target objects into desired positions for observation and analysis. In variations of the first specific example, the platform control module 133 can additionally or alternatively be configured to rotate the platform 130 about an axis parallel the platform to generate a distribution of focal lengths across the platform 130 for calibration of the relative locations of the optical sensor 150 and the target object(s) at the platform 130, thereby facilitating achievement of a desired focal length to analyze the target object(s). Variations of the first specific example can, however, be configured in any other suitable manner.

In a second specific example, as shown in FIGS. 2A and 2B, the platform 130 is situated intermediately between the first illumination subsystem 111 comprising a bright-field subsystem and the second illumination subsystem 121 comprising a fluorescence subsystem, wherein the first light source 112 of the first illumination subsystem 111 is configured to transmit light through a first set of optics 113 directly toward an imaging substrate 350 located inferior to the first illumination subsystem 111, at the platform 130. Light from the first light source 112 and transmitted through the imaging substrate 350 is then directed toward an optical sensor 150 at a location inferior to the platform 130, through a filter module 140. Furthermore, the second light source 122 of the second illumination subsystem 121 is configured to transmit light through a second set of optics 123 through at least one excitation filter 141 of the filter module, which reflects by a 90° angle at a dichroic mirror 142 of the filter module 140, through a focusing an optics module 160 and toward the imaging substrate 350 located superior to the second illumination subsystem 121, at the platform 130. In the second specific example, light from at least one target object at the imaging substrate 350 is then configured to be transmitted through the focusing and optics module 160, directly through the dichroic mirror 142, and toward the optical sensor 150 situated inferior to the filter module 140. In the second specific example, the platform 130 comprises eight guides 138 arranged in a 2×4 array, each guide 138 proximal to a retainer 139 that holds an imaging substrate 350 at the platform 130.

The platform 130 in the second specific example is further coupled to a platform control module 133 comprising a translation stage 334 configured to translate the platform 130 in coordinate directions parallel to the platform 130 (e.g., X and Y directions), by way of a translation controller 335 that automates translation of the translation stage 334. The translation stage 334 and translation controller 335 of the platform control module 133 can translate the platform in an X direction by a span of 9" and in a Y direction by a span of 5" in the second specific example. The platform control module 133 in the second specific example further includes an actuator configured to angularly displace the platform 130 about an axis parallel the platform to generate a distribution of focal lengths across the platform 130 for calibration of the relative locations of the optical sensor 150 and the target object(s) at the platform 130, thereby facilitating achievement of a desired focal length to analyze the target object(s). Variations of the second specific example can, however, be configured in any other suitable manner.

The system 100 of the preferred embodiment and variations thereof can be embodied and/or implemented at least in part as a machine configured to receive a computer-readable medium storing computer-readable instructions. The instructions are preferably executed by computer-executable components preferably integrated with the system 100 and one or more portions of the processor 220. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A system for detecting biological sample features comprising:
   a platform including a set of guides that receive a set of imaging substrates with a set of biological samples, wherein the set of guides is distributed about the platform in a first circular array;
   a set of filter modules superior to the platform, each of the set of filter modules including an excitation filter, an emission filter, and a dichroic mirror;
   a first light source, inferior to the platform, configured to transmit light toward a biological sample of the set of biological samples from a first direction;
   a second light source configured, in a first configuration, to transmit light through the excitation filter of a first of the set of filter modules, to be reflected from the dichroic mirror of the first of the set of filter modules, and to reach the biological sample from a second direction opposed to the first direction;
   a lens, coupled to a lens selector, that focuses light from the excitation filter onto a target object of the biological sample, and transmits light from the target object, through the dichroic mirror and the emission filter, toward an optical sensor;
   a platform control module configured to 1) rotate the platform about a first axis, associated with the first circular array and perpendicular to a broad surface of the platform and 2) translate the platform along a direction perpendicular to the first axis, into a first set of configurations that align each guide of the set of guides between the first light source and the lens;
   a filter stage, situated superior to the platform and wherein the set of filter modules is distributed about the filter stage in a second circular array, configured to rotate the set of filter modules about a second axis, parallel to the first axis, into a second set of configurations that aligns each of the set of filter modules to receive light from the second light source and to transmit light toward the optical sensor; and
   an optics manipulation module, including a translation stage coupled to an optical shaft concentrically aligned with the lens by way of the lens selector, configured to vertically translate the lens to facilitate focusing of the target object.

2. The system of claim 1, wherein the platform control module includes an actuator configured to translate the platform along two directions perpendicular to the first axis.

3. The system of claim 1, wherein the set of filter modules includes a set of excitation filters and a set of emission filters, including filters for at least two of: HEX-based assays, FAM-based assays, ROX-based assays, and Cy5-based assays.

4. The system of claim 1, wherein the platform control module is further configured to angularly displace the platform about a third axis parallel to the broad surface of the platform to generate a distribution of focal lengths across the platform in relation to the optical sensor, and wherein the system further includes a processor configured receive a dataset from the optical sensor to calibrate at least one of the optical sensor and the optics manipulation module, based upon a focal length of the distribution of focal lengths providing a maximum contrast level.

5. The system of claim 1, wherein lens selector is a revolving nosepiece configured to receive a set of lenses, and wherein the translation stage is coupled to a plate surrounding the optical shaft coupled to the revolving nosepiece, thereby enabling vertical translation of the lens.

6. The system of claim 1, wherein the platform further includes a fluidic manifold coupled to a fluid source and configured to distribute a fluid to at least one imaging substrate, and wherein the system further includes a processor configured to facilitate analysis of real-time fluid flow at the at least one imaging substrate based upon data generated by the optical sensor.

7. The system of claim 1, further including at least one imaging substrate, in the set of imaging substrates, including an array of parallel pores configured to capture a set of cells in single-cell format.

8. The system of claim 7, further including a processor configured to translate a series of characters, physically located proximal to a pore of the array of parallel pores and detectable using the optical sensor, into a binary number indicative of an address of the pore.

9. A system for detecting biological sample features comprising:
   a platform including a guide that holds an imaging substrate with a sample;
   a filter module including an excitation filter and an emission filter;
   a first light source configured to transmit light toward the sample at the platform from a first direction;
   a second light source configured to transmit light through the excitation filter to reach the sample from a second direction opposed to the first direction;
   a lens that focuses light from the excitation filter onto a target object of the sample, and transmits light from the target object, through the emission filter, toward an optical sensor superior to the filter module;
   a platform control module configured to rotate the platform about a first axis perpendicular to a broad surface of the platform into a first configuration that aligns at least one imaging substrate between the first light source and the lens,
      wherein the platform control module is further configured to angularly displace the platform about a third axis parallel to the broad surface of the platform to generate a distribution of focal lengths across the platform in relation to the optical sensor;
   a filter stage, situated superior to the platform, configured to rotate the filter module about a second axis, parallel to the first axis, into a second configuration that positions the filter module to receive light from the second light source and to transmit light toward the optical sensor;

an optics manipulation module configured to vertically translate the lens, wherein the optics manipulation module includes a lens selector coupled to the lens, an optical shaft coupled to the lens selector and concentrically aligned with the lens, and a translation stage coupled to the optical shaft; and a processor including a first module that coordinates actuation by the platform control module, the filter stage, and the optics manipulation module and a second module that calibrates at least one of the optical sensor and the optics manipulation module to facilitate focusing of the target object, based upon the distribution of focal lengths.

10. The system of claim 9, further including a set of guides distributed about the platform in a first circular array and a set of filter modules distributed about the filter stage in a second circular array, wherein the platform control module is configured to rotate the platform into a first set of configurations that align each guide of the set of guides between the first light source and the lens, and wherein the filter stage is configured to rotate the set of filter modules into a second set of configurations that align each filter module of the set of filter modules to receive light from the second light source and transmit light toward the optical sensor.

11. The system of claim 10, wherein the optical sensor is superior to the filter module, which is superior to the platform, which is superior to the first light source.

12. The system of claim 11, wherein the platform control module includes an actuator configured to translate the platform along two directions perpendicular to the first axis.

13. The system of claim 10, wherein the set of filter modules includes a set of excitation filters and a set of emission filters, including filters for at least two of: HEX-based assays, FAM-based assays, ROX-based assays, and Cy5-based assays.

14. The system of claim 9, wherein the filter module further includes dichroic mirror configured to bisect intersecting planes defined by the excitation filter and the emission filter, and wherein the system further includes a mirror configured to reflect light from the second light source into the filter module aligned in the second configuration, such that light from the second light source is reflected by 90° twice before reaching the imaging substrate.

15. The system of claim 9, further including a tag identifying system configured to communicate information regarding the sample at the imaging substrate to the processor, and a thermal control module that controls thermal parameters of at least one of the imaging substrate and the sample.

16. The system of claim 9, wherein the platform further includes a fluidic manifold coupled to a fluid source and configured to distribute a fluid to the imaging substrate, and wherein the processor further includes a third module configured to facilitate analysis of real-time fluid flow at the imaging substrate based upon data generated by the optical sensor.

17. The system of claim 9, further including the imaging substrate, wherein the imaging substrate includes an array of parallel pores configured to capture a set of cells in single-cell format.

18. The system of claim 17, wherein the processor further includes a fourth module configured to translate a series of characters, physically defined proximal to a pore of the array of parallel pores and detectable using the optical sensor, into a binary number indicative of an address of the pore.

* * * * *